(12) United States Patent
Corbett et al.

(10) Patent No.: US 7,250,418 B2
(45) Date of Patent: Jul. 31, 2007

(54) COMPOUNDS AS CRF₁ RECEPTOR ANTAGONISTS

(75) Inventors: Jeffrey W. Corbett, Niantic, CT (US); Michael Dalton Ennis, Chesterfield, MO (US); Kristine E. Frank, Worcester, MA (US); Jian-Min Fu, Burnaby (CA); Robert Louis Hoffman, San Marcos, CA (US); Patrick R. Verhoest, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 234 days.

(21) Appl. No.: 10/840,485

(22) Filed: May 6, 2004

(65) Prior Publication Data

US 2005/0038040 A1    Feb. 17, 2005

Related U.S. Application Data

(60) Provisional application No. 60/469,486, filed on May 9, 2003.

(51) Int. Cl.
| | |
|---|---|
| A61K 31/4965 | (2006.01) |
| C07D 239/02 | (2006.01) |
| C07D 401/00 | (2006.01) |
| C07D 403/00 | (2006.01) |
| C07D 405/00 | (2006.01) |

(52) U.S. Cl. .................. 514/255.05; 544/297; 544/405
(58) Field of Classification Search ..................... None
See application file for complete search history.

(56) References Cited

U.S. PATENT DOCUMENTS

| 5,872,136 | A | 2/1999 | Anthony et al. ............ 514/341 |
| 5,880,140 | A | 3/1999 | Anthony ..................... 514/333 |
| 5,883,105 | A | 3/1999 | Anthony ..................... 514/277 |
| 6,043,260 | A | 3/2000 | Chen et al. .................. 514/348 |
| 6,964,965 | B2 * | 11/2005 | Corbett et al. ........... 514/252.1 |

FOREIGN PATENT DOCUMENTS

| EP | 1097709 | 10/2000 |
| WO | 9735901 | 10/1997 |
| WO | 9736886 | 10/1997 |
| WO | 9736898 | 10/1997 |
| WO | 9829119 | 7/1998 |
| WO | 0160806 | 8/2001 |
| WO | 00160806 | 8/2001 |
| WO | 03045924 | 6/2003 |
| WO | 03091225 | 11/2003 |
| WO | 04024719 | 3/2004 |

OTHER PUBLICATIONS

Kehne and De Lombert, "Non-Peptidic CRF1 Receptor Antagonists for the Treatment of Anxiety, Depression and Stress Disorders" Current Drug Targets, vol. 1(5), pp. 467-493 (2002).*
Dautzenberg and Hauger, "The CRF peptide family and their receptors: yet more partners discovered" Trends in Pharmacological Sciences, vol. 23(2), pp. 71-77 (Feb. 2002).*
Richard B. Silverman, The Organic Chemistry of Drug Design and Drug Action, pp. 352-400. © 1992 Academic Press, Inc.*
Hans Bundgaard, Design of Prodrugs, p. 1. © 1985 Elsevier Science Publishers.*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*

* cited by examiner

*Primary Examiner*—Zachary C Tucker
(74) *Attorney, Agent, or Firm*—Steve T. Zelson; Eileen M. Ebel

(57) ABSTRACT

The present invention relates to compounds of Formula I,

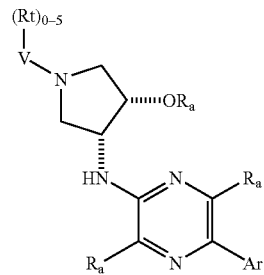

Formula I or a stereoisomer thereof, a pharmaceutically acceptable salt thereof, or a prodrug thereof. The compounds of the inventions are CRF₁ receptor antagonists. Compounds of the invention are useful for treating, in a warm-blooded animal, particularly a mammal, and more particularly a human, various disorders that are associated with CRF or CRF₁ receptors, or disorders the treatment of which can be effected or facilitated by antagonizing CRF₁ receptors.

12 Claims, No Drawings

COMPOUNDS AS CRF$_1$ RECEPTOR ANTAGONISTS

FIELD OF THE INVENTION

The present invention relates generally to compounds that bind to CRF receptors, and particularly to novel compounds as CRF$_1$ receptor antagonists and to the use thereof as a treatment for disorders that are associated with CRF or CRF$_1$ receptors.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, CRF is known to have a broad extrahypothalmic distribution in the CNS, contributing therein to a wide spectrum of autonomic behavioral and physiological effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is evidence that CRF plays a significant role in integrating the response in the immune system to physiological, psychological, and immunological stressors, in psychiatric disorders and neurological diseases including depression, anxiety-related disorders and feeding disorders, and in the etiology and pathophysiology of Alzheimers disease, Parkinson's disease, Huntington's disease, progressive supranuclear palsy and amyotrophic lateral sclerosis, as they relate to the dysfunction of CRF neurons in the central nervous system [J. E. Blalock, *Physiological Reviews* 69:1 (1989); J. E. Morley, *Life Sci.* 41:527 (1987); E. B. De Souze, *Hosp. Practice* 23:59 (1988)].

There is evidence that CRF plays a role in mood disorders. Mood disorders, also known as affective disorders, are well recognized in the art and include depression, including major depression, single episode depression, recurrent depression, child abuse induced depression, and postpartum depression; dysthemia; bipolar disorders; and cyclothymia. It was shown that in individuals afflicted with affective disorder, or major depression, the concentration of CRF in the cerebral spinal fluid (CSF) is significantly increased. [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders. Anxiety disorders are a group of diseases, recognized in the art, that includes phobic disorders, anxiety states, post-traumatic stress disorder, generalized anxiety disorder, social anxiety disorder, anxiety with co-morbid depressive illness, panic disorder, obsessive-compulsive disorder, and atypical anxiety disorders [The Merck Manual of Diagnosis and Therapy, 16$^{th}$ edition (1992)]. Emotional stress is often a precipitating factor in anxiety disorders, and such disorders generally respond to medications that lower response to stress. Excessive levels of CRF are known to produce anxiogenic effects in animal models [see, e.g., Britton et al., 1982; Berridge and Dunn, 1986 and 1987]. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn, *Regul. Peptides* 16:83 (1986)]. Studies using the putative CRF receptor antagonist α-helical ovine CRF (9-41) in a variety of behavioral paradigms demonstrates that the antagonist produces "anxiolytic-like" effects that are qualitatively similar to the benzodiazepines [C. W. Berridge and A. J. Dunn, *Horm. Behav.* 21:393 (1987), *Brain Research Reviews* 15:71 (1990); G. F. Koob and K. T. Britton, In: *Corticotropin-Releasing Factor: Basic and Clinical Studies of a Neuropeptide*, E. B. De Souza and C. B. Nemeroff eds., CRC Press p. 221 (1990)]. Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist Ro 15-1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)].

Use of CRF$_1$ antagonists for treating Syndrome X is described in EP 1097709 A2.

Use of CRF$_1$ antagonists for treating congestive heart failure is described in U.S. Pat. No. 6,043,260.

It has also been suggested that CRF$_1$ antagonists are useful for treating arthritis and inflammation disorders [E. L. Webster et al., *J. Rheumatol* 29:1252 (2002); E. P. Murphy et al., *Arthritis Rheum* 44:782 (2001)]; stress-related gastrointestinal disorders [K. E. Gabry et al., *Molecular Psychiatry* 7:474 (2002)]; and skin disorders [C. C. Zouboulis et al., *Proc. Natl. Acad. Sci.* 99:7148 (2002)].

It was disclosed recently that, in an animal model, stress-induced exacerbation of chronic contact dermatitis is blocked by a selective CRF$_1$ antagonist, suggesting that CRF$_1$ is involved in the stress-induced exacerbation of chronic contact dermatitis and that CRF$_1$ antagonist may be useful for treating this disorder [K. Kaneko et al., *Exp Dermatol,* 12:47 (2003)].

WO0160806 discloses compounds as antagonists of CRF$_1$ receptors.

WO9735901 discloses compounds as resins for use as high solid coatings. The following patents or patent applications disclose compounds as farnesyl protein transferase inhibitors: WO9829119, WO9736886, and WO9736898, and U.S. Pat. Nos. 5,872,136, 5,880,140, and 5,883,105.

It is an object of the invention to provide novel compounds.

It is another object of the invention to provide novel $CRF_1$ receptor antagonists.

It is another object of the invention to provide novel compounds as treatment of disorders or conditions that are associated with CRF or $CRF_1$ receptors, such as anxiety disorders, depression, and stress related disorders.

It is another object of the invention to provide a method of treating disorders or conditions that are associated with CRF or $CRF_1$ receptors, such as anxiety-related disorders, mood disorders, and stress related disorders.

It is yet another object of the invention to provide a pharmaceutical composition useful for treating disorders or conditions that are associated with CRF or $CRF_1$ receptors, such as anxiety-related disorders, mood disorders, and stress related disorders.

There are other objects of the invention which will be evident or apparent from the description of the invention in the specification of the application.

SUMMARY OF THE INVENTION

The present invention provides a compound of Formula I,

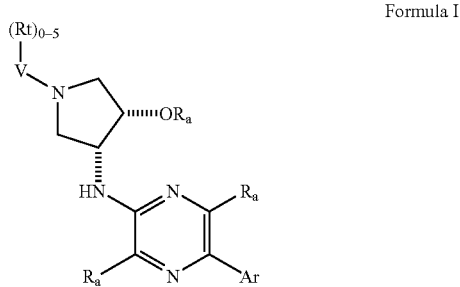

Formula I or a stereoisomer thereof, a pharmaceutically acceptable salt thereof, or a prodrug thereof, wherein in Formula I, Ar is selected from aryl, substituted aryl, heteroaryl, or substituted heteroaryl;

V is heteroaryl or phenyl, wherein heterocaryl and phenyl are optionally substituted with 1 to 5 of $R_t$;

$R_a$ each is independently selected from H, alkyl, cycloalkyl, haloalkyl, aryl, heteroaryl, or heterocycloalkyl, wherein alkyl, cycloalkyl, haloalkyl, aryl, heteroaryl, and heterocycloalkyl is optionally substituted with 1 to 5 of $R_t$, —Oalkyl, —S(O)$_m$R$_t$, NR$_t$R$_t$, oxo (=O), thione (=S), phenyl, heteroaryl, or heterocycloalkyl.

$R_t$ each is independently selected from H, halogen, —NO$_2$, —NH$_2$, —OH, —SH, —CN, —C(O)NH$_2$, —C(O)—NHalkyl, —C(O)Nalkylalkyl, —Oalkyl, —Ohaloalkyl, NHalkyl, Nalkylalkyl, —S(O)$_m$alkyl, SO$_2$NH$_2$, SO$_2$NHalkyl, SO$_2$Nalkylalkyl, alkyl, cycloalkyl, haloalkyl, phenyl, benzyl, heteroaryl, or heterocycloalkyl; and m is 0, 1 or 2.

In another aspect, the present invention provides a pharmaceutical composition comprising a compound of Formula I, a stereoisomer thereof, a pharmaceutically acceptable salt thereof, a prodrug thereof, or a pharmaceutically acceptable salt of a prodrug thereof. The compositions can be prepared in any suitable forms such as tablets, pills, powders, lozenges, sachets, cachets, elixirs, suspensions, emulsions, solutions, syrups, aerosols, and ointments.

The compounds of the inventions are $CRF_1$ receptor antagonists. Thus, in another aspect, the present invention provides a method of antagonizing $CRF_1$ receptors in a warm-blooded animal, comprising administering to the animal a compound of the invention at amount effective to antagonize $CRF_1$ receptors.

In still another aspect, the present invention provides a method for screening for ligands for $CRF_1$ receptors, which method comprises: a) carrying out a competitive binding assay with $CRF_1$ receptors, a compound of Formula I which is labeled with a detectable label, and a candidate ligand; and b) determining the ability of said candidate ligand to displace said labeled compound.

In still another aspect, the present invention provides a method for detecting $CRF_1$ receptors in a tissue comprising: a) contacting a compound of Formula I, which is labeled with a detectable label, with a tissue, under conditions that permit binding of the compound to the tissue; and b) detecting the labeled compound bound to the tissue.

In yet another aspect, the present invention provides a method of inhibiting the binding of CRF to $CRF_1$ receptors in vitro, comprising contacting a compound of the invention with a solution comprising cells expressing the $CRF_1$ receptor, such as IMR32 cells, wherein the compound is present in the solution at a concentration sufficient to inhibit the binding of CRF to the $CRF_1$ receptor.

Compounds of the invention are useful for treating, in a warm-blooded animal, particularly a mammal, and more particularly a human, various disorders that are associated with CRF or $CRF_1$ receptors, or disorders the treatment of which can be effected or facilitated by antagonizing $CRF_1$ receptors. Examples of such disorders include anxiety-related disorders (such as anxiety states, generalized anxiety disorder, social anxiety disorder, anxiety with co-morbid depressive illness, panic disorder, and obsessive-compulsive disorder, phobic disorders, post-traumatic stress disorder, and atypical anxiety disorders); mood disorders, also known as affective disorders (such as depression, including major depression, single episode depression, recurrent depression, child abuse induced depression, and postpartum depression; dysthemia; bipolar disorders; and cyclothymia); post-traumatic stress disorder; supranuclear palsy; immune suppression; drug or alcohol withdrawal symptoms; substance abuse disorder (e.g., nicotine, cocaine, ethanol, opiates, or other drugs); inflammatory disorders (such as rheumatoid arthritis and osteoarthritis); fertility problems including infertility; pain; asthma; psoriasis and allergies; phobias; sleep disorders induced by stress; pain perception (such as fibromyalgia); dysthemia; bipolar disorders; cyclothymia; fatigue syndrome; stress-induced headache; cancer; human immunodeficiency virus (HIV) infections; neurodegenerative diseases (such as Alzheimer's disease, Parkinson's disease and Huntington's disease); gastrointestinal diseases (such as ulcers, irritable bowel syndrome, Crohn's disease, spastic colon, diarrhea, and post operative ilius and colonic hypersensitivity associated by psychopathological disturbances or stress); eating disorders (such as anorexia and bulimia nervosa and other feeding disorders); hemorrhagic stress; stress-induced psychotic episodes; euthyroid sick syndrome; syndrome of inappropriate antidiarrhetic hormone (ADH); obesity; head traumas; spinal cord trauma; ischemic neuronal damage (e.g., cerebral ischemia such as cerebral hippocampal ischemia); excitotoxic neuronal damage; epilepsy; cardiovascular and heart related disorders (such as hypertension, tachycardia and congestive heart failure); stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); osteoporosis; psychosocial dwarfism, hypoglycemia, and skin disorders (such as acne, psoriasis, chronic contact dermatitis, and stress-exacerbated skin disorders). They are also useful for promoting smoking cessation and hair growth, or treating hair loss.

Thus, in yet a further aspect the present invention provides a method of treating a disorder, in warm-blooded animal, the treatment of which disorder can be effected or facilitated by antagonizing $CRF_1$ receptors, which method comprises administration to a patient in need thereof an effective amount of a compound of Formula I. In a particular embodiment the invention provides a method of treating disorders that manifest hypersecretion of CRF. Examples of disorders that can be treated with the compounds of the invention include generalized anxiety disorder; social anxiety disorder; anxiety; obsessive-compulsive disorder; anxiety with co-morbid depressive illness; panic disorder; and mood disorders such as depression, including major depression, single episode depression, recurrent depression, child abuse induced depression, postpartum depression, hair loss, and contact dermatitis. It is preferred that the warm-blooded animal is a mammal, and more preferred that the animal is a human.

DETAILED DESCRIPTION OF THE INVENTION

The present invention provides a compound of Formula I described above. Examples of particular compounds of the invention are provided in Examples 1–26 herein below, with each compound being identified by both a chemical name and a structural formula.

Compounds of the invention can be prepared using the reactions depicted in the following charts or variations thereof known to those skilled in the art. As illustrated in Chart A, the aminopyrazine A-II can be prepared from the suitably functionalized chloropyrazine A-I (see Chart C) by reaction with the appropriate pyrrolidinyl amine in the presence of a transition metal catalyst (e.g. palladium(II) acetate or tris(dibenzylideneacetone)dipalladium(0)), base (e.g. sodium or potassium tert-butoxide) in solvents such as but not limited to toluene, dimethyl formamide (DMF), or dioxane. (for example see Buchwald, S. L. et al *J. Org. Chem.* 2000, 65, 1158.). Halogenation of A-II can be accomplished by a number of methods well-known to those skilled in the art utilizing reagents such as N-chlorosuccinimide, N-bromosuccinimide, N-iodosuccinimide, bromine, iodine, pyridinium tribromide in solvents such as dichloromethane, acetic acid, DMF, etc, to give the halopyrazine A-III. Formation of the claimed compounds I is accomplished by a transition metal catalyzed coupling reaction A-III and an appropriate metalloaryl reagent such as aryl boronic acids (see for example Miyaura, N.; et al *Chem. Rev.* 1995, 95, 2457), aryl stannanes (see for example Mitchell, T. N. *Synthesis* 1992, 803), or aryl Grignards (see for example Miller, J. A. *Tetrahedron Lett.* 1998, 39, 7275). Alternatively, A-I can be coupled with a suitable metalloaryl reagent as described above to provide the arylpyrazine A-IV. Oxidation of the sterically less hindered nitrogen can be affected by using a variety of known oxidizing agents (eg, MCPBA, hydrogen peroxide), and the resulting N-oxide can be treated with phosphorous oxybromide to provide the bromopyrazine A-V. Reaction of the halogen with an amine as described above provides A-VII.

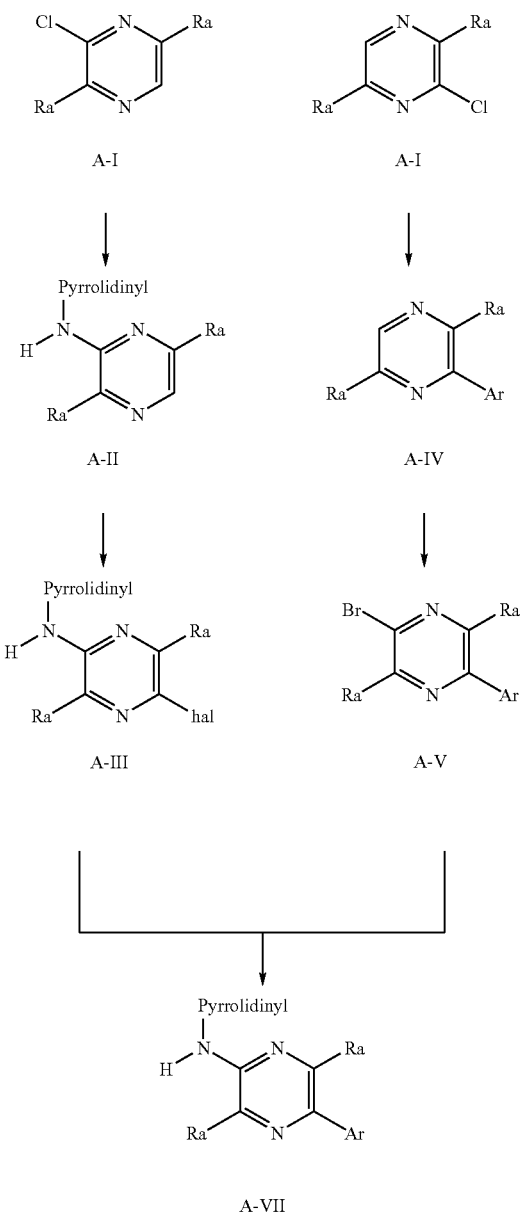

Another way of preparing the compounds of this invention is illustrated in Chart B. Dialkyl-dichloropyrazines B-I (see Chart C) can serve as the starting point for sequential displacement of one chlorine with the appropriate pyrrolidinyl amine (as described in Chart A) followed by biaryl formation with a suitable metalloaryl reagent (as described in Chart A) to afford B-II. In some instances, this sequence can also be conducted in the opposite order, i.e. biaryl formation followed by nucleophilic displacement by a pyrrolidinyl amine.

Chart B

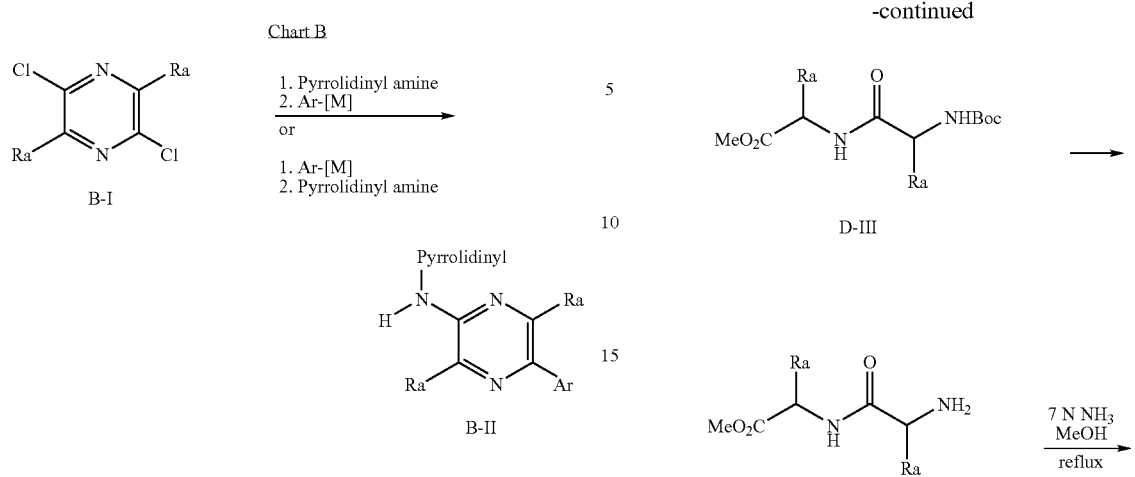

Chart C illustrates the preparation of mono- and dichloropyrazine A-I and B-I respectively when the Ra substituents are alkyl and equivalent. The reaction sequence shown below follows that described in *Chemical and Pharmaceutical Bulletin of Japan*, 1979, 27, 2027.

Chart C

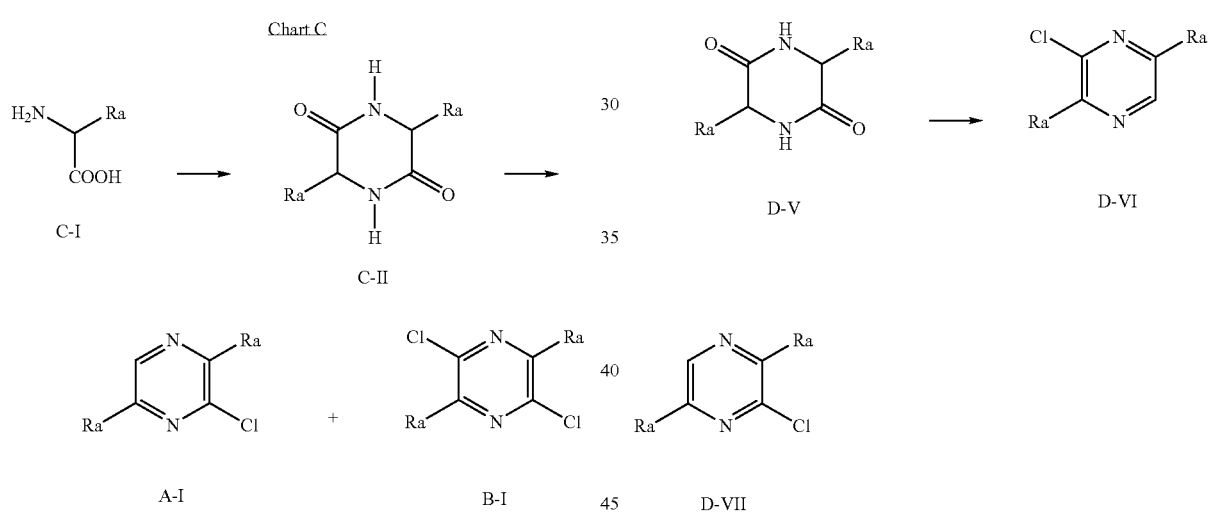

The preparation of unsymmetrically substituted pyrazines, when the two subtituents are not equivalent, is shown in Chart D. The synthesis commences with the coupling of a suitably protected amino acid, such as D-I, to an N-protected amino acid, such as D-II, using methods known to those skilled in the art. The N-protecting group is removed from D-III to afford D-IV. Cyclization of D-IV to D-V and the conversion of D-V into the regioisomeric chloro-pyrazines D-VI and D-VII proceed through standard methods (see *Chemical and Pharmaceutical Bulletin of Japan*, 1979, 27, 2027).

Chart D

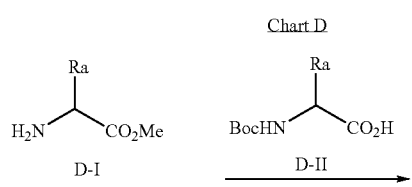

As illustrated in Chart I, the epoxide E-I is prepared by treatment of the commercially available olefin (benzyl 2,5-dihydro-1H-pyrrole-1-carboxylate) with MCPBA. The resultant epoxide can be opened in an asymmetric fashion with azide following the protocol of Jacobsen et al (*J. Org. Chem.* 1997, 62, 4197) or in a racemic fashion by treatment with ammonium hydroxide. Conversion of the trans amino alcohol to the cis follows the protocol of Jacobsen et al (*J. Org. Chem.* 1997, 62, 4197). Reaction of the pyrrolidine amine with a pyrazinyl chloride following the protocol of Buchwald et al (*J. Org. Chem.* 2000, 1158.) provides the desired aniline. Alkylation with NaH and an electorphile such as ethyl iodide provides the requisite ether. Halogenation with n-iodosuccinimide (NIS) affords the iodide compound E-VI. Alternatively, the amino-alcohol E-III could be prepared with a different protecting group or by another method by those skilled in the art.

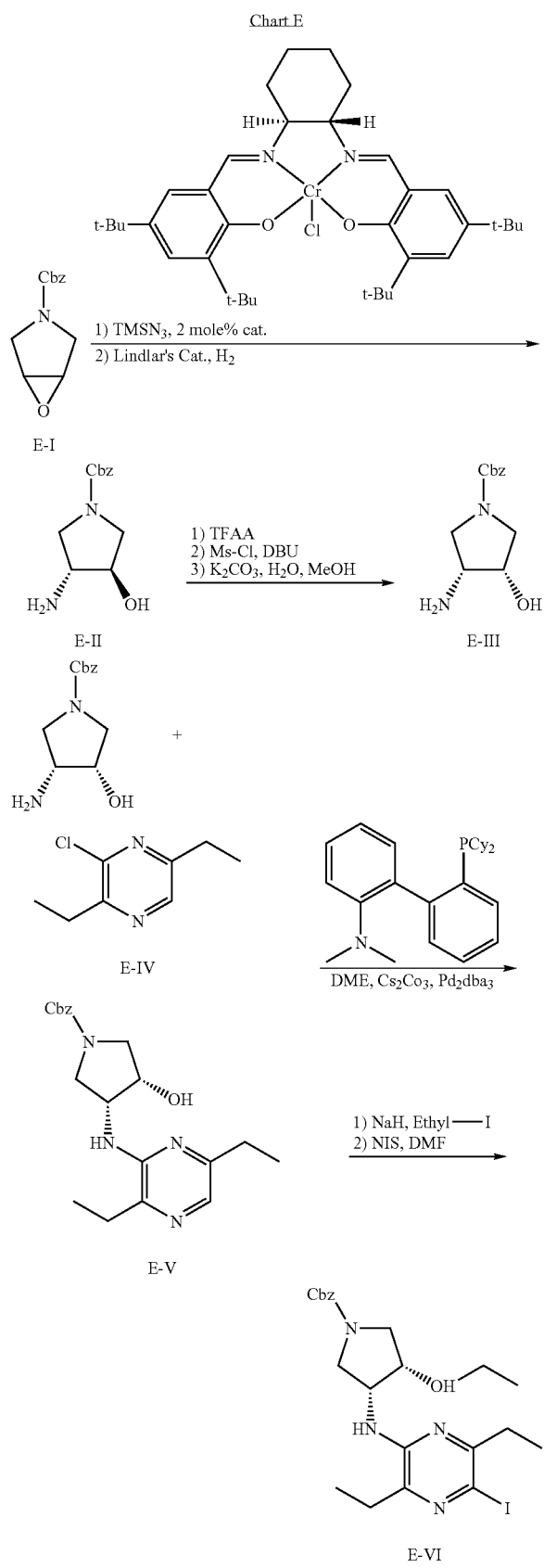

Another method for the preparation of compounds from this invention is disclosed in Chart F. Palladium mediate Suzuki or Negishi coupling of F-I and the appropriate aryl boronic acid or halide provides the biaryl products F-II. (see *Chem. Rev.* 1995, 95, 2457. or *Tetrahedron* 1998, 54, 263.) Removal of the CBZ group via hydrogenation, transfer hydrogenation or treatment with a Lewis Acid provides the amine F-III. Subsequent N-arylation following the protocol of Buchwald, Hartwig or Nolan provided the desired heteraryl products F-IV. (see *J. Org. Chem.* 2000, 1158, *Org. Lett.* 2000, 1423. or *J. Org. Chem.* 2001, 7729.

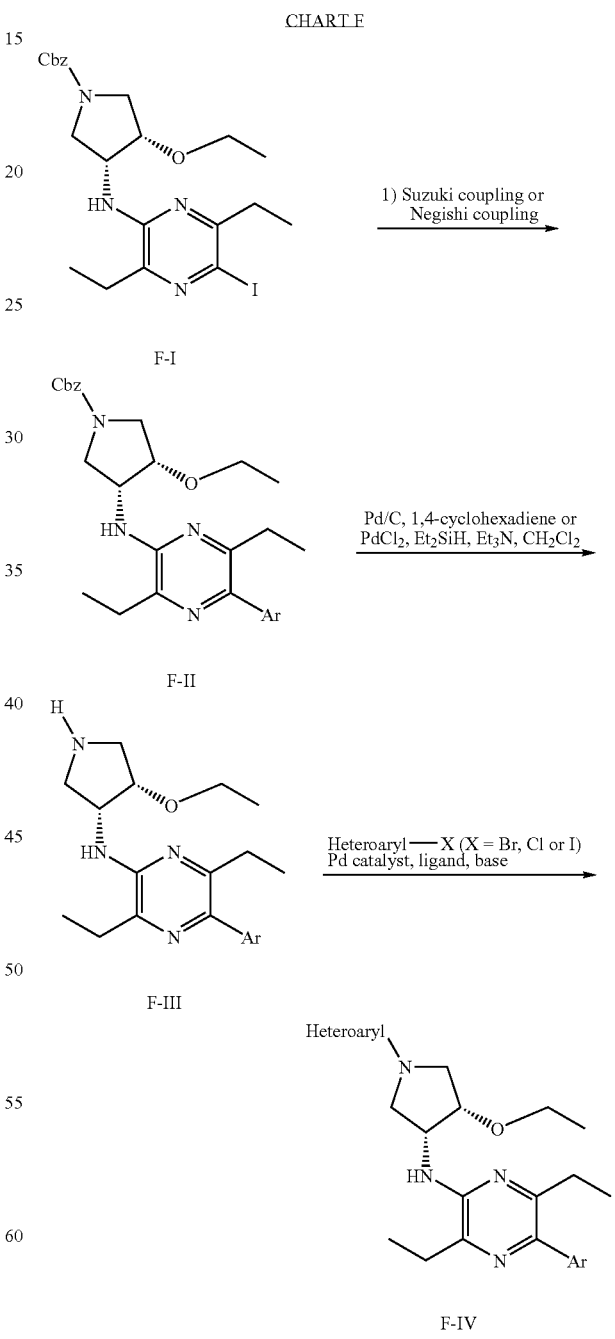

It should be understood that compounds provided herein can have one or more asymmetric centers or planes, and all chiral (enantiomeric and diastereomeric) and racemic forms of the compound are included in the present invention. Many geometric isomers of olefins, C=N double bonds, and the like can also be present in the compounds, and all such stable isomers are contemplated in the present invention. Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by a asymmetric synthesis route enabling the preparation of enantiomerically enriched material. The present invention encompasses all possible tautomers of the compounds represented by Formula I.

The present invention also encompasses pharmaceutically acceptable salts of compounds of Formula I. Examples of pharmaceutically acceptable salts are salts prepared from inorganic acids or organic acids, such as inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like.

Pharmaceutically acceptable salts of the compounds of the invention can be prepared by conventional chemical methods. Generally, such salts are, for example, prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, the disclosure of which is hereby incorporated by reference.

In another aspect, the present invention provides a prodrug of a compound of Formula I. The prodrug is prepared with the objective(s) of improved chemical stability, improved patient acceptance and compliance, improved bioavailability, prolonged duration of action, improved organ selectivity (including improved brain penetrance), improved formulation (e.g., increased hydrosolubility), and/ or decreased side effects (e.g., toxicity). See e.g. T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs include, but are not limited to, compounds derived from compounds of Formula I wherein hydroxy, amine or sulfhydryl groups, if present, are bonded to any group that, when administered to the subject, cleaves to form the free hydroxyl, amino or sulfhydryl group, respectively. Selected examples include, but are not limited to, biohydrolyzable amides and biohydrolyzable esters and biohydrolyzable carbamates, carbonates, acetate, formate and benzoate derivatives of alcohol and amine functional groups.

The prodrug can be readily prepared from the compounds of Formula I using methods known in the art. See, e.g. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172–178, 949–982 (1995). For example, the compounds of Formula I can be transformed into prodrugs by converting one or more of the hydroxy or carboxy groups into esters.

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I, and $^{125}$I. Compounds of Formula I that contain the aforementioned isotopes and/or other isotopes of other atoms are within the scope of the invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly useful in PET (positron emission tomography), and $^{125}$I isotopes are particularly useful in SPECT (single photon emission computed tomography); all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures by substituting a isotopically labeled reagent for a non-isotopically labeled reagent.

The compounds of Formula I are antagonists at the $CRF_1$ receptor, capable of inhibiting the specific binding of CRF to $CRF_1$ receptor and antagonizing activities associated with $CRF_1$ receptor. The effectiveness of a compound as a CRF receptor antagonist may be determined by various assay methods. A compound of Formula I may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "Ki" value. $IC_{50}$ and Ki values are calculated using standard methods known in the art, such as with the non-linear curve-fitting program GraphPad Prism (GraphPad Software, San Diego, Calif.). A compound is considered to be active if it has an Ki of less than about 10 micromolar (μM) for the inhibition of $CRF_1$ receptors. The binding affinity of the compounds of Formula I expressed as Ki values generally ranges from about 0.5 nanomolar to about 10 micromolar. Preferred compounds of Formula I exhibit Ki value of 1 micromolar or less, more preferred compounds of Formula I exhibit Ki values of less than 100 nanomolar, still more preferred compounds of Formula I exhibit Ki values of less than 10 nanomolar.

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Alternatively, adenylate cyclase activity or cAMP production can be assessed in a 96/384-well format utilizing the cAMP competitive ELISA system from Applied Biosystems (Bedford, Mass.) according to the protocols provided. Briefly, a fixed amount of diluted cAMP-alkaline phosphatase conjugate (cAMP-AP) is added to 96 or 386-well plates containing samples from cells that were stimulated with CRF in the presence or absence of inhibitors. Anti-cAMP antibody is added to the mixture and incubated for 1 hr. Following successive wash steps, the chemiluminescent substrate/enhancer solution is added which then produces a light signal that can be detected using a microplate scintillation counter such as the Packard TopCount. cAMP produced by the cells will displace the cAMP-AP conjugate from the antibody yielding a decrease of detectable signal. An example of the CRF-stimulated adenylate cyclase activity assay is provided in Example C below.

Thus, in another aspect, the present invention provides a method of antagonizing $CRF_1$ receptors in a warm-blooded animal, comprising administering to the animal a compound of the invention at amount effective to antagonize $CRF_1$ receptors. The warm-blooded animal is preferably a mammal, and more preferably a human.

In another aspect, the present invention provides a method of treating a disorder in a warm-blooded animal, which disorder manifests hypersecretion of CRF, or the treatment of which disorder can be effected or facilitated by antagonizing $CRF_1$ receptors, comprising administering to the animal a therapeutically effective amount of a compound of the invention. The warm-blooded animal is preferably a mammal, and more preferably a human.

In another aspect, the present invention provides a method for screening for ligands for $CRF_1$ receptors, which method comprises: a) carrying out a competitive binding assay with $CRF_1$ receptors, a compound of Formula I which is labeled with a detectable label, and a candidate ligand; and b) determining the ability of said candidate ligand to displace said labeled compound. Assay procedure for competitive binding assay is well known in the art, and is exemplified in Example A.

In another aspect, the present invention provides a method for detecting $CRF_1$ receptors in tissue comprising: a) contacting a compound of Formula I, which is labeled with a detectable label, with a tissue, under conditions that permit binding of the compound to the tissue; and b) detecting the labeled compound bound to the tissue. Assay procedure for detecting receptors in tissues is well known in the art.

In another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the $CRF_1$ receptor. An example of the cell line that expresses the $CRF_1$ receptor and can be used in the in vitro assay is IMR32 cells known in the art.

Compounds of Formula I, or a stereoisomer, a pharmaceutically acceptable salt, or a prodrug thereof, are useful for the treatment of a disorder in a warm-blooded animal, which disorder manifests hypersecretion of CRF, or the treatment of which disorder can be effected or facilitated by antagonizing $CRF_1$ receptors. Examples of such disorders are described herein above. They are also useful for promoting smoking cessation or promoting hair growth.

Thus, in still another aspect, the present invention provides a method of treating a disorder described herein above, comprising administering to a warm-blooded animal a therapeutically effective amount of a compound of the invention. The warm-blooded animal is preferably a mammal, particularly a human.

Particular disorders that can be treated by the method of the invention preferably include the following: anxiety-related disorders, such as generalized anxiety disorder, social anxiety disorder, anxiety with co-morbid depressive illness, obsessive-compulsive disorder, and panic disorder, anxiety states, phobic disorders, anxiety with co-morbid depressive illness, obsessive-compulsive disorder, post-traumatic stress disorder, and atypical anxiety disorders;mood disorders such as depression, including major depression, single episode depression, recurrent depression, child abuse induced depression, and postpartum depression, bipolar disorders, post-traumatic stress disorder, dysthemia, and cyclothymia; substance abuse disorder (e.g., nicotine, cocaine, ethanol, opiates, or other drugs); inflammatory disorders such as rheumatoid arthritis and osteoarthritis; gastrointestinal diseases such as irritable bowel syndrome, ulcers, Crohn's disease, spastic colon, diarrhea, and post operative ilius and colonic hypersensitivity associated by psychopathological disturbances or stress; and skin disorders such as acne, psoriasis, and chronic contact dermatitis.

Particular disorders that can be treated by the method of the invention more preferably include the following: anxiety-related disorders; mood disorders; inflammation disorders; and chronic contact dermatitis.

Particular disorders that can be treated by the method of the invention even more preferably include anxiety-related disorders, particularly generalized anxiety, and mood disorders, particularly major depression.

The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active-ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

A compound of this invention can be administered to treat the above disorders by means that produce contact of the active agent with the agent's site of action in the body of a mammal, such as by oral, topical, dermal, parenteral, or rectal administration, or by inhalation or spray using appripropriate dosage forms. The term "parenteral" as used herein includes subcutaneous injections, intravenous, intramuscular, intrasternal injection or infusion techniques. The compound can be administered alone, but will generally be administered with a pharmaceutically acceptable carrier, diluent, or excipient.

Thus in yet another aspect, the present invention provides a pharmaceutical composition comprising a compound of Formula I, a stereoisomer thereof, a pharmaceutically acceptable salt thereof, or a prodrug thereof, or a pharmaceutically acceptable salt of the prodrug thereof. In one embodiment, the pharmaceutical composition further comprises a pharmaceutically acceptable carrier, diluent, or excipient therefore. A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, $17^{th}$ ed., Mack Publishing Company, Easton, Pa., 1985, the contents of which are incorporated herein by reference.

Compositions intended for oral use may be in the form of tablets, troches, lozenges, aqueous or oily suspensions, dispersible powders or granules, emulsion, hard or soft capsules, or syrups, or elixirs, and can be prepared according to methods known to the art. Such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and a delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long aliphatic alcohols, for example heptadecaethyleneoxycetanol, or condensation products of ethylene oxide with partial esters derived from fatty acids and a hexital such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more sweetening agents, such as sucrose or saccharin.

Oily suspensions may be formulated by suspending the active ingredients in a vegetable oil, for example arachis oil, olive oil, soybean oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occuring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

Suppositories for rectal administration of a compound of the invention can be prepared by mixing the compound with a suitable non-irritating excipient, which is solid at ordinary temperatures but liquid at the rectal temperature and will therefore melt in the rectum to release the drug. Examples of such materials are cocoa butter and polyethylene glycols.

Pharmaceutical compositions may be in the form of a sterile injectable aqueous or oleaginous suspension. This suspension may be formulated according to the known art using those suitable dispersing or wetting agents and suspending agents, which have been mentioned above. The sterile injectable solution or suspension may be formulated in a non-toxic parentally acceptable diluent or solvent, for example as a solution in 1,3-butanediol. Among the acceptable vehicles and solvents that may be employed are water, Ringers's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms suitable for administration generally contain from about 1 mg to about 100 mg of active ingredient per unit. In these pharmaceutical compositions, the active ingredient will ordinarily be present in an amount of about 0.5 to 95% by weight based on the total weight of the composition. Examples of dosage forms for administration of compounds of the invention includes the following: (1) Capsules. A large number of units capsules are prepared by filling standard two-piece hard gelatin capsules each with 100 mg of powdered active ingredient, 150 mg lactose, 50 mg cellulose, and 6 mg magnesium stearate; (2) Soft Gelatin Capsules. A mixture of active ingredient in a digestible oil such as soybean, cottonseed oil, or olive oil is prepared and injected by means of a positive displacement into gelatin to form soft gelatin capsules containing 100 mg of the active ingredient. The capsules were washed and dried; (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

In still another aspect, the present invention provides an article of manufacture comprising: a) a packaging material; b) a pharmaceutical agent comprising a compound of the invention contained within said packaging material; and c) a label or package insert which indicates that said pharmaceutical agent can be used for treating a disorder described above.

DEFINITIONS AND CONVENTIONS

The following definitions are used throughout the application, unless otherwise described.

The term "halogen" means a group selected from —F, —Cl, —Br, and —I.

The term "alkyl" means both straight and branched chain hydrocarbon moieties having 1–10 carbon atoms, optionally containing one or more double or triple bonds.

The term "cycloalkyl" means a monocyclic or bicyclic, non-aromatic hydrocarbon moiety, having 3–10 carbon atoms and optionally containing 1 to 2 double bonds.

The term "haloalkyl" means an alkyl moiety having 1 to (2v+1) independently-selected halogen substituent(s) where v is the number of carbon atoms in the moiety.

The term "aryl" means either phenyl or naphthyl.

The term "substituted aryl" means an aryl group substituted with 1–5 substituents independently selected from halogen, —$NO_2$, —CN, —$R_a$, —$OR_a$, —$S(O)_mR_a$, $NR_aR_a$, —$C(O)NR_aR_a$, —$C(S)NR_aR_a$ —$S(O)_2NR_aR_a$, —$NR_aS(O)_m$ $R_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, and —$OC(O)ORa$.

The term "heteroaryl" means a radical of a monocyclic aromatic ring containing five or six ring atoms consisting of carbon and 1 to 4 heteroatoms each selected from the group consisting of non-peroxide O, S, and N, with appropriate bonding to satisfy valence requirements, wherein the attachment may be via a ring carbon or ring N where a N is present. The term "heteroaryl" also includes a radical of a fused bicyclic heteroaromatic ring having eight to ten ring atoms consisting of carbon and 1 to 6 heteroatoms each selected from non-peroxide O, S, N, with appropriate bonding to satisfy valence requirements, wherein the attachment may be via a ring carbon or ring N where a N is present. Examples of heteroaryl include thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl.

The term "substituted heteroaryl" means a heteroaryl group having 1–5 substituents independently selected from halogen, —$NO_2$, —CN, —$R_a$, —$OR_a$, —$S(O)_mR_a$, —$NR_aR_a$, —$C(O)NR_aR_a$, —$C(S)NR_aR_a$—$S(O)_2NR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, and —$OC(O)OR_a$.

The term "heterocycloalkyl" means a 4 to 8 membered non-aromatic monocyclic ring or bicyclic ring, wherein at least one carbon atom is replaced with a heteromember selected from oxygen, nitrogen, —NH—, or —$S(O)_m$— wherein m is zero, 1, or 2, wherein the ring attachment can occur at either a carbon or nitrogen atom. A heterocycloalkyl can optionally contain 1–3 double bonds. Examples of heterocycloalkyl includes tetrahydrofuranyl, tetrahydropyranyl, morpholinyl, pyrrolidinyl, piperidinyl, piperazinyl, [2.2.1]-azabicyclic rings, [2.2.2]-azabicyclic rings, [3.3.1]-azabicyclic rings, quinuclidinyl, azetidinyl, azetidinonyl, oxindolyl, dihydroimidazolyl, and pyrrolidinonyl.

The term "substituted heterocycloalkyl" means a heterocycloalkyl group having 1–5 substituents independently selected from halogen, —$NO_2$, —CN, oxo (=O), thione (=S), —$R_a$, —$OR_a$, —$S(O)_mR_a$, —$NR_aR_a$, —$C(O)NR_aR_a$, —$C(S)NR_aR_a$ —$S(O)_mNR_aR_a$, —$NR_aS(O)_mR_a$, —$NR_aC(O)OR_a$, —$OC(O)NR_aR_a$, —$NR_aC(O)NR_aR_a$, —$NR_aC(S)NR_aR_a$, —$C(O)OR_a$, —$C(S)OR_a$, and —$OC(O)OR_a$.

The term "pharmaceutically acceptable," unless otherwise described, refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" refers to a salt which retains the biological effectiveness and properties of the compounds of this invention and which is not biologically or otherwise undesirable.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate" or "racemic mixture" refer to a mixture of equal parts of enantiomers.

The term "prodrug" means compounds that are transformed in vivo to yield a compound of Formula I. The transformation may occur by various mechanisms, such as through hydrolysis in blood.

The term "therapeutically effective amount," "effective amount," "therapeutic amount," or "effective dose" is meant that amount sufficient to elicit the desired pharmacological or therapeutic effects, thus resulting in effective prevention or treatment of the disease.

The phrases "a compound of the invention," "a compound of the present invention," "compounds of the present invention," or "a compound in accordance with Formula I" and the like, refer to compounds of Formula I, or stereoisomers thereof, pharmaceutically acceptable salts thereof, or prodrugs thereof, or pharmaceutically acceptable salts of a prodrug of compounds of Formula I.

The terms "treatment," "treat," "treating," and the like, are meant to include both slowing or reversing the progression of a disorder, as well as curing the disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

EXAMPLES

Without further elaboration, it is believed that one skilled in the art can, using the preceding description, practice the present invention to its fullest extent. The following examples are provided to illustrate the invention and are not to be construed as limiting the invention in scope or spirit to the specific procedures described in them. The numerical preparations and examples are provided to illustrate the preparation of compounds of the invention and Examples A–D are provided to illustrate biological assays that can be used for determining the biological properties of the compounds of the inventions. Those skilled in the art will promptly recognize appropriate variations from the procedures described in the examples.

Preparation 1

Preparation of benzyl 6-oxa-3-azabicyclo[3.1.0]hexane-3-carboxylate

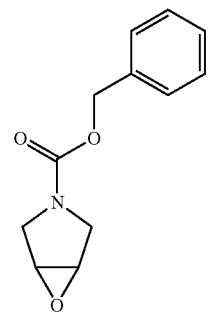

To a solution of the olefin (10.0 g, 49 mmol) in $CH_2Cl_2$ (250 ml, 0.2M) was added MCPBA (22 g, 2.0 eq.). The reaction was stirred for 48 h and 200 ml of saturated sodium thiosulfate was added. After 20 min, the layers were separated and the organic layer was washed with 2N NaOH (2×100 ml). The organic layer was dried $MgSO_4$, filtered and concentrated to provide the title compound as an oil (10.79 g, 99%): 1H NMR (300 MHz, CDCl3) δ 7.35, 5.13, 3.93–3.84, 3.71, 3.43–3.38; IR (liq.) 2209 (w), 2068 (w), 1958 (w), 1706 (s), 1455, 1448, 1428 (s), 1397 (s), 1364, 1327 (s), 1214, 1206, 1107 (s), 848 (s), 699, $cm^{-1}$ Anal. Calcd for $C_{12}H_{13}N\ O_3$: C, 65.74; H, 5.98; N, 6.39. Found: C, 65.45; H, 6.07; N, 5.99.

Preparation 2

Preparation of benzyl (3R,4R)-3-(Azido)-4-[(trimethylsilyl)oxy]pyrrolidine-1-carboxylate

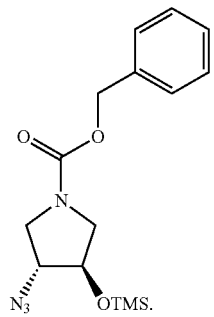

To benzyl 6-oxa-3-azabicyclo[3.1.0]hexane-3-carboxylate (10.4 g, 48 mmole) was added $TMSN_3$ (6.65 ml, 1.05 eq.) and 1S,2S-(−)-[1,2-cyclohexanediamino-N,N'-bis(3,5-di-t-butylsalicylidene)]chromium(III) chloride (STREM 24-0851) (904 mg, 0.03 eq.). The reaction was stirred for 18 h under $N_2$. The red oil was used as is in the next step. $^1H$ NMR (400 MHz, $CDCl_3$) δ 7.18 (m, 5 H), 4.98 (s, 2 H), 3.99 (m, 1 H), 3.69 (m, 1 H), 3.61–3.51 (m, 2 H), 3.31–3.05 (m, 2 H).

Preparation 3

Preparation of benzyl (3R,4R)-3-amino-4-hydroxypyrrolidine-1-carboxylate

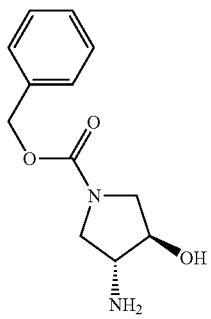

Benzyl (3R,4R)-3-(2lambda~5~-triaza-1,2-dienyl)-4-[(trimethylsilyl)oxy]pyrrolidine-1-carboxylate (23.6 g) in MeOH (250 ml, 0.3M) was treated with trifluoro acetic acid (TFA) (15 ul) for 1.5 hr. Lindlar's catalyst (10 g) was added under 1 atmosphere of $H_2$. It was stirred for 6 days. (Another batch of Lindlar's catalyst 5 g was added on the $4^{th}$ day). The Pd catalyst was filtered through celite. The filtrate was concentrated, diluted with $Et_2O$ (250 ml) and 1N HCl (250 ml). The separated 1N HCl phase was basified with NaOH (solid) to pH 12. It was extracted with $CH_3Cl:iPrOH$ (9:1 mixture 4×300 ml) and EtOAC (3×300 ml). It was dried ($MgSO_4$) and used as is. $^1$H NMR ($CDCl_3$) δ 3.22 (m, 1 H), 3.38 (m, 2 H), 3.78 (m, 2 H), 4.02 (m, 1 H), 5.15 (s, 2 H), 7.37 (m, 5 H);

Preparation 4

Preparation of benzyl (3R,4S)-3-amino-4-hydroxypyrrolidine-1-carboxylate

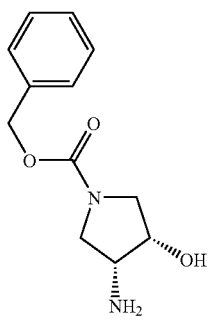

A 50 ml oven-dried r.b.flask was charged with benzyl (3R,4R)-3-amino-4-hydroxypyrrolidine-1-carboxylate (4.235 g, 17.93 mmol) and dissolved in 60 ml of tetrahydrofuran (THF). Trifluoroacetic anhydride (2.54 ml, 17.93 mmol) and TEA (3 ml, 21.52 mmol) were added sequentially at 0° C. The rxn was allowed to warm to r.t., and stirred for O/N. The reaction was diluted with $H_2O$ (250 ml), extracted with 250 ml ($CHCl_3:iPrOH$ 9:1 mixture, ×4), dried ($MgSO_4$), filtered, concentrated in vacuo.

This crude trifluoroamide product (confirmed by LC-MS) was dissolved in 90 ml of $CH_2Cl_2$ (0.2M) and cooled to 0° C. under $N_2$ followed by addition of TEA (21.52 mmol, 3 ml) and MsCl (1.63 ml, 19.72 mmol). The reaction was stirred for 15 min at 0° C. and 1 hr at r.t followed by addition of DBU (5.39 ml, 53.79 mmol) with subsequent stirring overnight. The reaction mixture was filtered through silica and washed with (80% EtOAc in Heptane,) 800 ml. The filtrate was collected and concentrated.

The oxazoline was hydrolyzed by addition of $K_2CO_3$ (14.87 g) in 80 ml MeOH/40 ml $H_2O$ for 18 hr. It was reduced in volume and extracted with (9:1 $CHCl_3:iPrOH$) 200 ml×5. The combined organic solvent was dried ($K_2CO_3$), filtered, concentrated, purified by biotage chromatography (1% to 5% MeOH in $CH_2Cl_2$, 0.5% $NH_4OH$) to give the title compound as a solid. $^1$H NMR ($CDCl_3$) δ 3.22 (m, 1 H), 3.38 (m, 2 H), 3.79 (m, 2 H), 4.02 (m, 1 H), 5.15 (s, 2 H), 7.40 (m, 5 H); IR (diffuse reflectance) 3374, 2949, 2316 (w), 1966 (w), 1947 (w), 1686 (s), 1450 (s), 1423 (s), 1354, 1321, 1144, 1096, 1084, 765, 695, $cm^{-1}$ HRMS (FAB) calcd for $C_{12}H_{16}N_2O_3$+H 237.1239. found 237.1236. Specific Rotation (25 C D)=−17 (c 0.97, chloroform).

Preparation 5

Preparation of benzyl (3R,4S)-3-[(3,6-diethylpyrazin-2-yl)amino]-4-hydroxypyrrolidine-1-carboxylate

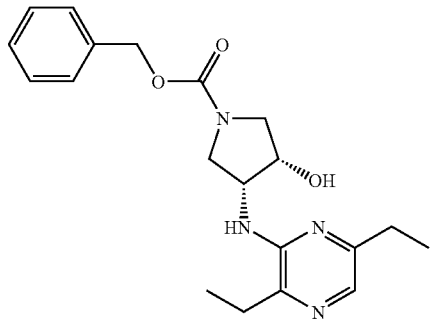

To an 250 ml r.b-flask was sequentially added benzyl (3R,4S)-3-amino-4-hydroxypyrrolidine-1-carboxylate (4.9714 g, 21.04 mmol), chloride (3.949 g, 23.15 mmol), $Pd_2(dba)_3$ (10 mol %, 1.926 g), 2-dicyclohexylphosphino-2'-(N,N-dimethylamino)biphenyl (20 mol %, 1.656 g), and DME (110 ml). $Cs_2CO_3$ (9.57 g) was then added and the reaction mixture was stirred at 80° C. for 20 hr. It was cooled, diluted with $Et_2O$ (100 ml), poured into $NaHCO_3$ (80 ml), extracted with $CH_2Cl_2$ (150 ml×3), dried ($MgSO_4$), and concentrated. Purification via biotage chromatography (35% EtOAc in heptane) provided the title compound. $^1$H NMR ($CDCl_3$) δ 1.28 (m, 6 H), 2.65 (m, 4 H), 3.36 (m, 1 H), 3.63 (m, 1 H), 3.73 (m, 1 H), 4.00 (m, 1 H), 4.51 (m, 1 H), 4.64 (m, 1 H), 4.80 (m, 1 H), 5.18 (s, 2 H), 7.38 (m, 6 H), 7.74 (d, 1H); IR (liq.) 2969, 2344 (w), 1996 (w), 1952 (w), 1703 (s), 1691 (s), 1546, 1499 (s), 1449 (s), 1426 (s), 1395, 1359 (s), 1175, 1133, 1095, $cm^{-1}$ HRMS (FAB) calcd for $C_{20}H_{26}N_4O_3$+H 371.2083. found 371.2089.

Preparation 6

Preparation of benzyl (3R,4S)-3-[(3,6-diethylpyrazin-2-yl)amino]-4-ethoxypyrrolidine-1-carboxylate

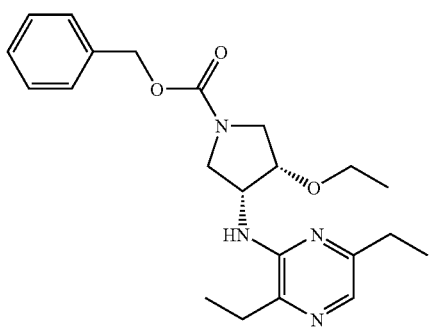

To a solution of benzyl (3R,4S)-3-[(3,6-diethylpyrazin-2-yl)amino]-4-hydroxypyrrolidine-1-carboxylate (17.70 g, 47.8 mmole) in DMF (0.3M) at 0° C. under $N_2$ was added NaH portionwise (2.48 g, 1.3 eq.). After 15 min, ethyl iodide (4.93 ml, 1.3 eq.) was added dropwise. After 2 h, the reaction mixture was quenched with brine (200 ml), extracted 2×200 ml ethyl acetate, dried $MgSO_4$, filtered and concentrated. Vacuum chromatography was run on a 1 L frit funnel eluting with 20–40% ethyl acetate/heptane to give 14.64 g (77%) of an oil. 1H NMR (400 MHz, $CDCl_3$) δ 7.68, 7.37, 5.19, 5.08, 4.72, 4.06, 3.98, 3.74–3.56, 3.45, 3.26, 2.63, 1.34–1.22, IR (liq.) 2971 (s), 2936, 2340 (w), 1950 (w), 1709 (s), 1546 (s), 1499 (s), 1464 (s), 1448 (s), 1422 (s), 1395 (s), 1350 (s), 1173, 1129 (s), 1097 (s) $cm^{-1}$ HRMS (ESI) calcd for $C_{22}H_{30}N_4O_3+H_1$ 399.2396. found 399.2392. Specific Rotation (25 C D)=−50 (c 0.55, 0.1N HCl).

Preparation 7

Preparation of benzyl (3R,4S)-3-[(3,6-diethyl-5-iodopyrazin-2-yl)amino]-4-ethoxypyrrolidine-1-carboxylate

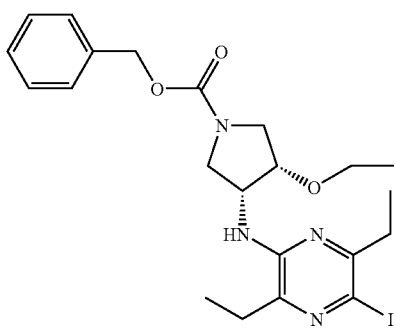

Following the procedure for the preparation of methyl (3R,4S)-3-[(3,6-diethyl-5-iodopyrazin-2-yl)amino]-4-ethoxypyrrolidine-1-carboxylate but substituting benzyl (3R,4S)-3-[(3,6-diethylpyrazin-2-yl)amino]-4-ethoxypyrrolidine-1-carboxylate provided the title compound as an oil: $^1$H NMR (400 MHz, $CDCl_3$) δ) 7.30–7.25, 5.06, 4.96, 4.53, 3.96, 3.86, 3.64–3.47, 3.35, 3.25–3.13, 2.68, 2.51, 1.20–1.12; IR (liq.) 2972, 2338 (w), 1949 (w), 1708 (s), 1554 (s), 1537 (s), 1475 (s), 1456 (s), 1447 (s), 1421 (s), 1394 (s), 1351 (s), 1165, 1126, 1097 (s) $cm^{-1}$ HRMS (ESI) calcd for C22H29N4O3I+H1 25.1364. found 525.1359. Anal. Calcd for $C_{22}H_{29}IN_4O_3$: C, 50.39; H, 5.57; N, 10.68. Found: C, 50.48; H, 5.60; N, 10.44.

Preparation 8

Preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate

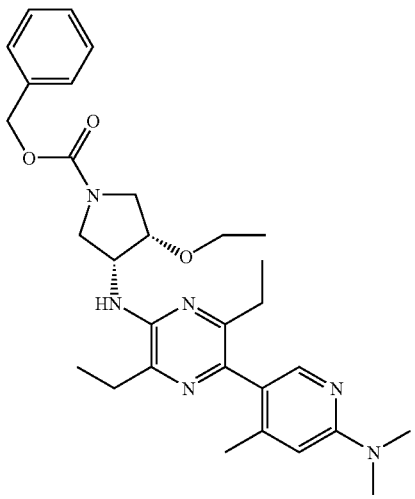

To a solution of benzyl (3R,4S)-3-[(3,6-diethyl-5-iodopyrazin-2-yl)amino]-4-ethoxypyrrolidine-1-carboxylate (1.93 g) in ethylene glycol dimethyl ether (18.4 ml) was added 2-dimethyl amino-4-methyl-5-pyridyl boronic acid (1.32 g, 2 eq.) and Palladium tetrakis (425 mg, 0.1 eq.) and 2 N sodium carbonate (3.7 ml). The reaction mixture was heated at 80° C. for 18 h, poured into saturated sodium bicarbonate (100 ml), extracted 2×100 ml of ethyl acetate, dried $MgSO_4$, filtered and concentrated. Purification via biotage MPLC eluting with 20–70% ethyl acetate/heptane provided the title compound as an oil (760 mg, 39%): $^1$H NMR (400 MHz, $CDCl_3$) δ) 7.98, 7.40–7.34, 6.45, 5.18–5.06, 4.74, 4.09, 3.97, 3.76–3.30, 3.12, 2.68, 2.53, 2.11, 1.31–1.24, 1.14; IR (diffuse reflectance) 2971, 2932, 2453 (w), 2340 (w), 1949 (w), 1708 (s), 1605 (s), 1566 (s), 1490 (s), 1445 (s), 1418 (s), 1395 (s), 1350 (s), 1127, 1095 $cm^{-1}$ HRMS (ESI) calcd for $C_{30}H_{40}N_6O_3+H_1$ 533.3240. found 533.3240.

Preparation 9

Preparation of benzyl (3R,4S)-3-{[5-(2,4-dichlorophenyl)-3,6-diethylpyrazin-2-yl]amino}-4-ethoxypyrrolidine-1-carboxylate

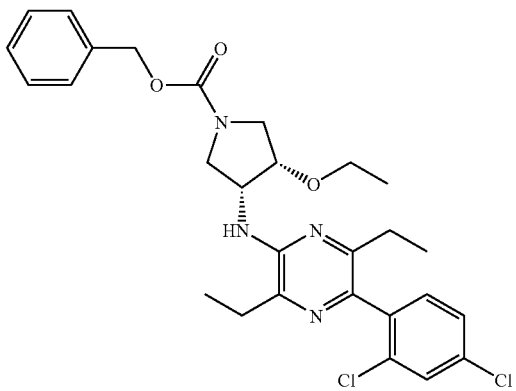

Following the procedure for the preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate but substituting 2,4-dichloro phenyl boronic acid and making non-critical variations provided the title compound as a oil: $^1$H NMR (400 MHz, CDCl$_3$) δ) 7.49, 7.40–7.25, 5.20–5.13, 4.76, 4.11, 3.98, 3.73–3.60, 3.51–3.31, 2.70, 2.47, 1.31–1.24, 1.15; IR (liq.) 2972, 2342 (w), 1948 (w), 1709 (s), 1567, 1552, 1498 (s), 1470 (s), 1449 (s), 1420 (s), 1397 (s), 1350, 1126, 1100 (s), 1080, cm$^{-1}$

Preparation 10

Preparation of benzyl (3R,4S)-3-{[5-(2-chloro-4-methoxyphenyl)-3,6-diethylpyrazin-2-yl]amino}-4-ethoxypyrrolidine-1-carboxylate

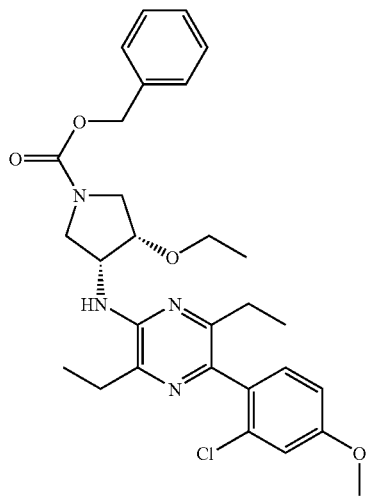

Following the procedure for the preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate but substituting 2-chloro-4-methoxy phenyl boronic acid and making non-critical variations provided the title compound as a oil: $^1$H NMR (DMSO-d$_6$) δ) 1.04, 1.16, 2.38, 2.68, 3.34, 3.40, 3.54, 3.70, 3.82, 4.18, 4.62, 5.10, 5.95, 6.98, 7.10, 7.26, 7.38; IR (diffuse reflectance) 2971, 2934, 2350 (w), 2338 (w), 2063 (w), 1949 (w), 1710 (s), 1568, 1482 (s), 1419 (s), 1397 (s), 1348, 1287, 1228, 1096, cm$^{-1}$ HRMS (FAB) calcd for C$_{29}$H$_{35}$ClN$_4$O$_4$+H 539.2425. found 539.2436. Anal. Calcd for C$_{29}$H$_{35}$ClN$_4$O$_4$: C, 64.61; H, 6.54; N, 10.39; Cl, 6.58. Found: C, 64.30; H, 6.56; N, 10.26.

Preparation 11

Preparation of benzyl (3R,4S)-3-{[3,6-diethyl-5-(6-methoxy-2-methylpyridin-3-yl)pyrazin-2-yl]amino}-4-ethoxypyrrolidine-1-carboxylate

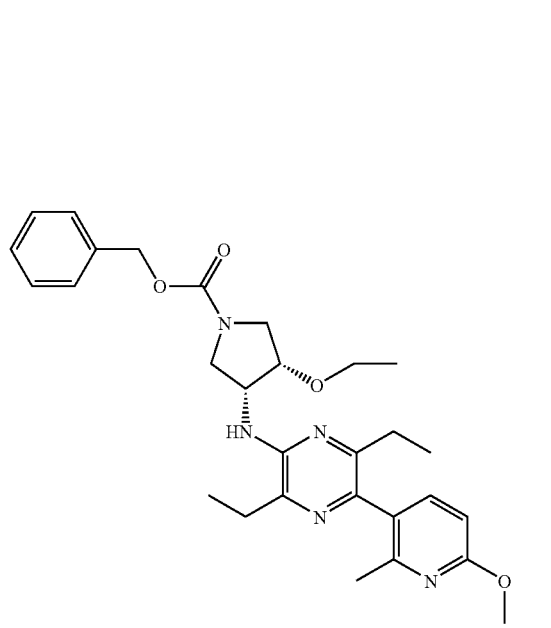

Following the procedure for the preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate but substituting 6-methoxy-2-methylpyridin-3-ylboronic acid provided the title compound as an oil: 1H NMR (400 MHz, CDCl$_3$) δ) 7.41–7.36, 6.64, 5.17–5.15, 4.78, 4.11, 4.02–3.97, 3.73–3.35, 2.70, 2.46, 2.28, 1.32–1.21, 1.13; IR (liq.) 2236 (w), 2018 (w), 1949 (w), 1709 (s), 1596, 1565, 1499, 1474 (s), 1420 (s), 1396, 1360, 1350, 1304 (s), 1126, 1097 cm$^{-1}$ HRMS (ESI) calcd for C$_{29}$H$_{37}$N$_5$O$_4$+H$_1$ 520.2924. found 520.2924.

Preparation 12

Preparation of benzyl (3R,4S)-3-{[3,6-diethyl-5-(4-methoxy-2-methylphenyl)pyrazin-2-yl]amino}-4-ethoxypyrrolidine-1-carboxylate

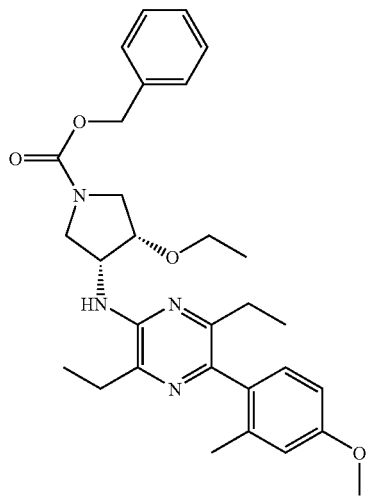

Following the procedure for the preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate and but substituting 2-methyl-4-methoxy-phenyl boronic acid provided the title compound as an amorphous solid. $^1$H NMR (CDCl$_3$) δ 1.04, 1.21, 2.04, 2.40, 2.65, 3.22~3.26, 3.41, 3.52~3.68, 3.75, 3.94, 4.03, 4.68, 5.08, 6.70, 6.74, 7.02, 7.28~7.32; IR (liq.) 2971 (s), 2339 (w), 2166 (w), 2082 (w), 1957 (w), 1708 (s), 1564 (s), 1482 (s), 1420 (s), 1395 (s), 1349 (s), 1242 (s), 1169 (s), 1125 (s), 1096 (s) cm$^{-1}$ HRMS (ESI) calcd for C30H38N4O4+H1 519.2971. found 519.2974.

Preparation 13

Preparation of 6-methoxy-3-nitro-2-(trifluoromethyl)pyridine

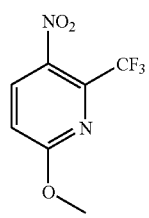

2-Chloro-6-methoxy-3-nitropyridine (5 g) was heated with CuI (6.05 g), KF(anhydrous, 3.0 g), methyl 2-chloro-2,2-difluoroacetate(6.8 ml) in DMF (28 ml) at 130° C. for 8 hrs. After cooling, it was poured into 1:9 mixture of NH$_4$OH/NH$_4$Cl(100 ml), stirred until homogeneous and extracted with Ethyl acetate. The organic layer were combined, washed with brine and dried (MgSO$_4$), The flash column chromatography (SiO$_2$, 1~3% EtOAc in heptane) yielded 3.90 g (65%). $^1$H NMR (CDCl$_3$) δ 4.02, 6.96, 8.10; IR (liq.) 2389 (w), 2254 (w), 2196 (w), 2163 (w), 2017 (w), 1605 (s), 1586 (s), 1538 (s), 1482 (s), 1340 (s), 1290 (s), 1261 (s), 1205 (s), 1180 (s), 1155 (s) cm$^{-1}$ Anal. Calcd for C$_7$H$_5$F$_3$N$_2$O$_3$: C, 37.85; H, 2.27; N, 12.61; F, 25.66. Found: C, 37.68; H, 2.29; N, 12.30.

Preparation 14

Preparation of 6-methoxy-2-(trifluoromethyl)pyridin-3-amine

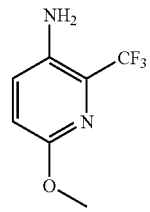

To a solution of 6-methoxy-3-nitro-2-(trifluoromethyl)pyridine (3.61 g) in 95% Ethyl alcohol (162 ml) was added tin(II) chloride dihydrate. It was heated to 70° C. for 3 hr. After it was cooled to room temperature, it was poured over ice water and adjusted to pH 11 with 2N NaOH. It was stirred well with ethyl acetate and filtered through celite. The organic phase was separated, washed with brine, dried (MgSO$_4$), filtered and concentrated. The flash column chromatography (SiO$_2$, 3~8% EtOAc in heptane) gave the title compounds (2.20 g, 71%). $^1$H NMR (CDCl$_3$) δ 3.81, 6.70, 7.05; $^{19}$F NMR (CDCl$_3$) δ 65.73; IR (liq.) 2434 (w), 2389, 2272, 2229, 2174, 1488 (s), 1436 (s), 1426 (s), 1276 (s), 1170 (s), 1102 (s, b), 1050 (s), 1024 (s), 740 (s), 658 (s) cm$^{-1}$ HRMS (ESI) calcd for C7H7N2OF3+H1 193.0589. found 193.0581. Anal. Calcd for C$_7$H$_7$F$_3$N$_2$O: C, 43.76; H, 3.67; N, 14.58; F, 29.66. Found: C, 43.61; H, 3.49; N, 14.49.

Preparation 15

Preparation of 3-iodo-6-methoxy-2-(trifluoromethyl)pyridine

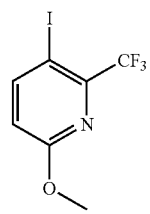

6-methoxy-2-(trifluoromethyl)pyridin-3-amine (1 g) was dissolved in H$_2$SO$_4$ (3 ml) and a dropwise addition of sodium nitrite (718 mg) in H$_2$O (3 ml) was made to reaction mixture at 0° C. After 2 hour of stirring at 0° C., it was raised to room temperature. Potassium iodide (1.73 g) in H$_2$O (3 ml) was added to the reaction mixture in a drop-wise fashion. It was heated to 60° C. for 3 hour. It was extracted with ethyl acetate, washed with sodium thiosulfate solution (Sat.), dried (MgSO$_4$), filtered and concentrated. The flash column chromatography (SiO$_2$, 1~5% EtOAc in heptane) gave the title compounds (3.47 g, 67%). $^1$H NMR (CDCl$_3$) δ 3.97, 6.68; 8.08; $^{19}$F NMR (CDCl$_3$) δ 66.16; IR (liq.) 2478

(w), 2364 (w), 2230 (w), 2173 (w), 2026 (w), 1585 (s), 1471 (s), 1422 (s), 1396 (s), 1338 (s), 1280 (s), 1238 (s), 1200 (s), 1180, 1140 (s) cm$^{-1}$ Anal. Calcd for $C_7H_5F_3INO$: C, 27.75; H, 1.66; N, 4.62; F, 18.81. Found: C, 27.93; H, 1.80; N, 4.62.

Preparation 16

Preparation of benzyl (3R,4S)-3-({3,6-diethyl-5-[6-methoxy-2-(trifluoromethyl)pyridin-3-yl]pyrazin-2-yl}amino)-4-ethoxypyrrolidine-1-carboxylate

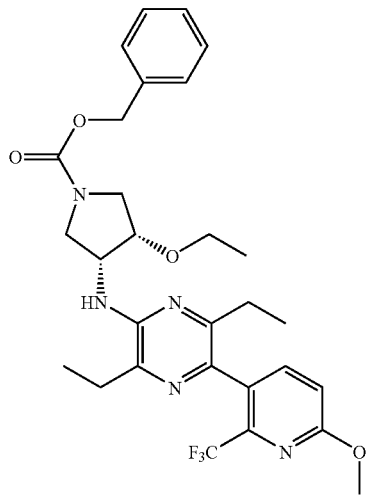

To a solution of 3-iodo-6-methoxy-2-(trifluoromethyl)pyridine (162 mg, 3 eq.) and Zinc chloride (0.5 M THF, 9 eq.) in THF (2.67 ml) under $N_2$ at −78° C. was added t-butyl lithium (9 eq.). After 5 min, the reaction mixture was warmed to ambient temperature and cannula'd into a flask containing benzyl (3R,4S)-3-[(3,6-diethyl-5-iodopyrazin-2-yl)amino]-4-ethoxypyrrolidine-1-carboxylate (120 mg) and palladium tetrakis (31 mg). The reaction mixture was heated at reflux for 16 h, poured into saturated sodium bicarbonate (50 ml), extracted 3×50 ml of $CH_2Cl_2$, dried $MgSO_4$, filtered and concentrated. Purification via MPLC chromatography eluting with 20–45% ethyl acetate/heptane afforded the title compound as an amorphous solid (63 mg, 53%):

$^1$H NMR (CDCl$_3$) δ 1.05, 1.18, 2.34, 2.63, 3.21~3.32, 3.38, 3.57, 3.65, 3.90, 3.95, 4.03, 4.66, 5.08, 5.15, 6.88, 7.28~7.32, 7.46; IR (liq.) 2346 (w), 2178 (w), 2026 (w), 1951 (w), 1709 (s), 1480 (s), 1421 (s), 1400 (s), 1344 (s), 1279 (s), 1239 (s), 1192 (s), 1176 (s), 1137 (s), 1097 (s) cm$^{-1}$ HRMS (ESI) calcd for C29H34N5O4F3+H1 574.2641. found 574.2644. Anal. Calcd for $C_{29}H_{34}F_3N_5O_4$: C, 60.72; H, 5.97; N, 12.21; F, 9.94. Found: C, 60.88; H, 6.12; N, 12.01.

Preparation 17

Preparation of benzyl (3R,4S)-3-{[5-(2,6-dimethoxypyridin-3-yl)-3,6-diethylpyrazin-2-yl]amino}-4-ethoxypyrrolidine-1-carboxylate

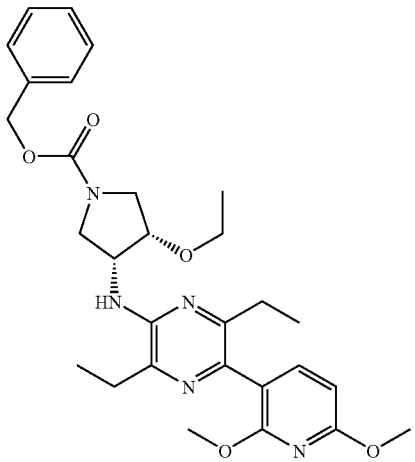

Following the procedure for the preparation of benzyl (3R,4S)-3-({5-[6-(dimethylamino)-4-methylpyridin-3-yl]-3,6-diethylpyrazin-2-yl}amino)-4-ethoxypyrrolidine-1-carboxylate and but substituting 2,6-dimethoxypyridin-3-ylboronic acidprovided the title compound as an amorphous solid. $^1$H NMR (400 MHz, CDCl$_3$) δ) 7.53, 7.40–7.28, 6.42, 5.17, 5.07, 4.76, 4.15, 4.01, 3.87, 3.92, 3.76–3.64, 3.50–3.33, 2.70, 2.51, 1.32–1.24, 1.18; IR (diffuse reflectance) 2416 (w), 2349 (w), 2325 (w), 2265 (w), 2184 (w), 1709 (s), 1602 (s), 1579 (s), 1475 (s), 1458 (s), 1419 (s), 1397 (s), 1376 (s), 1312 (s), 1101 (s) cm$^{-1}$ HRMS (ESI) calcd for C29H37N5O5+H1 536.2873. found 536.2867. Anal. Calcd for $C_{29}H_{37}N_5O_5$: C, 65.03; H, 6.96; N, 13.07. Found: C, 64.71; H, 7.03; N, 12.82.

Preparation 18

Preparation of 5-(2,4-dichlorophenyl)-N-[(3R,4S)-4-ethoxypyrrolidin-3-yl]-3,6-diethylpyrazin-2-amine

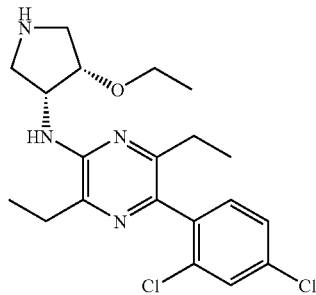

To a solution of benzyl (3R,4S)-3-{[5-(2,4-dichlorophenyl)-3,6-diethylpyrazin-2-yl]amino}4-ethoxypyrrolidine-1-carboxylate (8.60 g, 15.8 mmole) in $CH_2Cl_2$ (0.1M, 158 ml) under $N_2$ was added Palladium chloride (279 mg, 1.58 mmole) and triethyl amine (3.29 ml, 1.5 eq.). Triethylsilane (3.78 ml, 1.5 eq.) was added dropwise over 15 min. After one hour an additional 8.74 ml of triethylsilane was added dropwise. After 2 additional hours, the reaction mixture was filtered through celite. Trifluoroacetic acid (8 ml) was added and the reaction mixture was stirred for 30 min. Quenched to pH 10 with 2N NaOH and extracted 3×300 ml of $CH_2Cl_2$, dried $MgSO_4$, filtered and concentrated. Vacuum chromatography was run on a 1 L frit funnel with 5–15% MeOH/$CH_2Cl_2$ with 0.5% $NH_4OH$ to give 5.95 g (92%) of an oil. $^1H$ NMR (400 MHz, $CDCl_3$) δ) 7.49, 7.33–7.26, 5.38, 4.54, 4.07, 3.68, 3.52, 3.22, 2.95, 2.71, 2.46, 1.29, 1.15; HRMS (FAB) calcd for $C_{20}H_{26}Cl_2N_4O+H$ 409.1562. found 409.1567. Anal. Calcd for $C_{20}H_{26}Cl_2N_4O$: C, 58.68; H, 6.40; N, 13.69. Found: C, 58.42; H, 6.43; N, 13.50.

Preparation 19

Preparation of 5-(2-chloro-4-methoxyphenyl)-N-[(3R,4S)-4-ethoxypyrrolidin-3-yl]-3,6-diethylpyrazin-2-amine

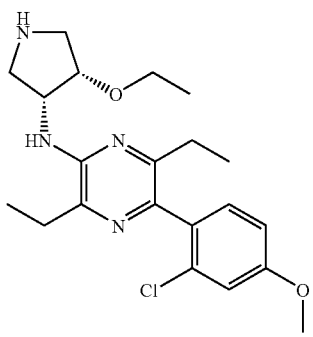

Following the procedure for the preparation of 5-(2,4-dichlorophenyl)-N-[(3R,4S)-4-ethoxypyrrolidin-3-yl]-3,6-diethylpyrazin-2-amine but substituting benzyl (3R,4S)-3-{[5-(2-chloro-4-methoxyphenyl)-3,6-diethylpyrazin-2-yl]amino}-4-ethoxypyrrolidine-1-carboxylate and making non-critical variations provided the title compound as an oil: $^1H$ NMR ($CDCl_3$) δ 1.15, 1.22–1.34, 2.45, 2.71, 2.89, 3.06, 3.22, 3.41, 3.51, 3.65, 3.85, 4.51, 5.32, 6.88, 7.02, 7.24; IR (liq.) 2971 (s), 2935, 2496 (w), 2446, 2402 (w), 2261 (w), 2072 (w), 1605, 1566 (s), 1483 (s), 1441, 1395, 1287 (s), 1230 (s), 1045 (s) $cm^{-1}$ HRMS (ESI) calcd for C21H29N4O2Cl+H1 405.2057. found 405.2044.

Preparation 20

Preparation of N-[(3R,4S)-4-ethoxypyrrolidin-3-yl]-3,6-diethyl-5-(6-methoxy-2-methylpyridin-3-yl)pyrazin-2-amine

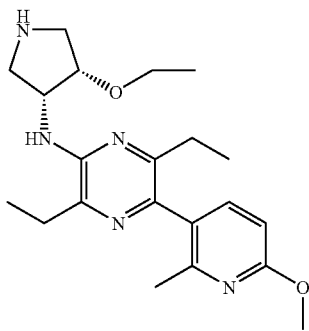

To a solution of benzyl (3R,4S)-3-{[3,6-diethyl-5-(6-methoxy-2-methylpyridin-3-yl)pyrazin-2-yl]amino}-4-ethoxypyrrolidine-1-carboxylate (1.35 g) in ethanol (26 ml) was added 1,4 cyclohexadiene (2.45 ml, 10 eq.) and 10% Pd/C (1.5 g). The reaction mixture stirred 2 h, was filtered through celite and concentrated. Purification via MPLC chromatography eluting with 2–6% methanol/$CH_2Cl_2$ with 0.5% ammonium hydroxide afforded the title compound as an amber oil (870 mg, 87%): 1H NMR (400 MHz, $CDCl_3$) δ) 7.41, 6.64, 5.34–5.32, 4.52, 4.05, 3.97, 3.68, 3.53, 3.43, 3.22, 3.15, 2.92, 2.70, 2.46, 2.29, 1.32–1.25, 1.14; IR (liq.) 2972, 2935, 2408 (w), 2238 (w), 2019 (w), 1971 (w), 1596, 1563 (s), 1499, 1474 (s), 1426, 1394, 1304 (s), 1251, 1042 $cm^{-1}$ HRMS (ESI) calcd for $C_{21}H_{31}N_5O_2+H_1$ 386.2556. found 386.2544.

Preparation 21

Preparation of 5-[6-(dimethylamino)-4-methylpyridin-3-yl]-N-[(3R,4S)-4-ethoxypyrrolidin-3-yl]-3,6-diethylpyrazin-2-amine

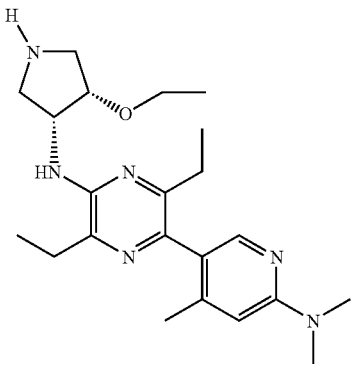

Following the procedure for the preparation of N-[(3R,4S)-4-ethoxypyrrolidin-3-yl]-3,6-diethyl-5-(6-methoxy-2-methylpyridin-3-yl)pyrazin-2-amine but substituting benzyl (3R,4S)-3-({5-[6-(dimethylamino)-4-methylpyridin-3-yl]-3,6-diethyl pyrazin-2-yl}amino)-4-ethoxypyrrolidine-1-carboxylate provided the title compound as an oil: $^1H$ NMR (400 MHz, $CDCl_3$) δ) 7.98, 6.45, 5.30, 4.51, 4.04, 3.67, 3.52, 3.43, 3.19, 3.12, 2.92, 2.69, 2.51, 2.11, 1.32–1.25, 1.15; IR (liq.) 2971 (s), 2933 (s), 2873 (s), 2345 (b), 1946 (w), 1607 (s), 1565 (s), 1516 (s), 1490 (s), 1395 (s), 1373, 1207, 1163, 1125, 1080 $cm^{-1}$ HRMS (ESI) calcd for $C_{22}H_{34}N_6O+H_1$ 399.2872. found 399.2877.

Preparation 22

Preparation of N-[(3R,4S)-4-ethoxypyrrolidin-3-yl]-3,6-diethyl-5-(4-methoxy-2-methylphenyl)pyrazin-2-amine

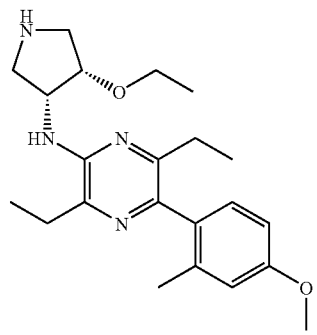

Following the procedure for the preparation of N-[(3R,4S)-4-ethoxypyrrolidin-3-yl]-3,6-diethyl-5-(6-methoxy-2-methylpyridin-3-yl)pyrazin-2-amine but substituting benzyl (3R,4S)-3-{[3,6-diethyl-5-(4-methoxy-2-methylphenyl)pyrazin-2-yl]amino}-4-ethoxypyrrolidine-1-carboxylate provided the title compound as an amber oil. $^1$H NMR (CDCl$_3$) δ 1.12, 1.30, 2.12, 2.46, 2.72, 2.92–3.14, 3.36, 3.52, 3.63–3.82, 3.84, 4.18–4.24, 4.71–4.86, 5.11–5.22, 6.78, 6.83, 7.09; IR (diffuse reflectance) 2970 (s), 2933 (s), 2875, 2835, 2493 (b), 2467 (b), 2439 (b), 2353, 2338 (w), 1568 (s), 1563, 1482 (s), 1397 (s), 1393, 1242 (s) cm$^{-1}$ HRMS (ESI) calcd for C22H32N4O2+H1 385.2603. found 385.2603.

Preparation 23

Preparation of N-[(3R,4S)-4-ethoxypyrrolidin-3-yl]-3,6-diethyl-5-[6-methoxy-2-(trifluoromethyl)pyridin-3-yl]pyrazin-2-amine

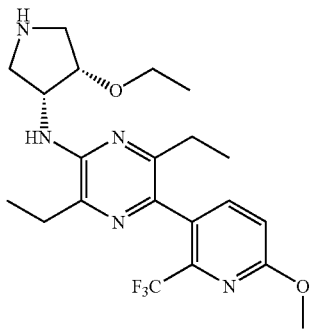

Following the procedure for the preparation of N-[(3R,4S)-4-ethoxypyrrolidin-3-yl]-3,6-diethyl-5-(6-methoxy-2-methylpyridin-3-yl)pyrazin-2-amine but substituting benzyl (3R,4S)-3-({3,6-diethyl-5-[6-methoxy-2-(trifluoromethyl)pyridin-3-yl]pyrazin-2-yl}amino)-4-ethoxypyrrolidine-1-carboxylate provided the title compound as an amber oil. $^1$H NMR (CDCl$_3$) δ 1.13, 1.28, 2.41, 2.69, 3.14, 3.37, 3.51, 3.66~3.75, 4.04, 4.16, 4.69, 5.29, 6.96, 7.54; IR (liq.) 2975 (s), 2417 (b), 2177 (b), 2029 (w), 1923 (w), 1609 (s), 1565 (s), 1479 (s), 1400 (s), 1341 (s), 1278 (s), 1239 (s), 1192 (s), 1177 (s), 1138 (s) cm$^{-1}$.

Preparation 24

Preparation of 5-(2,6-dimethoxypyridin-3-yl)-N-[(3R,4S)-4-ethoxypyrrolidin-3-yl]-3,6-diethylpyrazin-2-amine

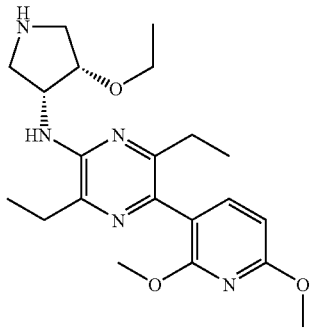

Following the procedure for the preparation of N-[(3R,4S)-4-ethoxypyrrolidin-3-yl]-3,6-diethyl-5-(6-methoxy-2-methylpyridin-3-yl)pyrazin-2-amine but substituting benzyl (3R,4S)-3-{[5-(2,6-dimethoxypyridin-3-yl)-3,6-diethylpyrazin-2-yl]amino}-4-ethoxypyrrolidine-1-carboxylate provided the title compound as an amber oil. $^1$H NMR (400 MHz, CDCl$_3$) δ) 7.53, 6.42, 5.29, 4.52, 4.04, 3.98, 3.92, 3.66, 3.51, 3.40, 3.21, 3.12, 2.91, 2.72, 2.48, 1.28, 1.18; IR (liq.) 2972, 2418 (w), 2184 (w), 2036 (w), 1993 (w), 1603, 1581 (s), 1564, 1477 (s), 1423, 1395, 1376 (s), 1313 (s), 1233, 1022 cm$^{-1}$ HRMS (ESI) calcd for C21H31N5O3+H1 402.2505. found 402.2516.

Example 1

Preparation of 5-(2,4-dichlorophenyl)-N-[(3R,4S)-4-ethoxy-1-(1,3-thiazol-2-yl)pyrrolidin-3-yl]-3,6-diethylpyrazin-2-amine

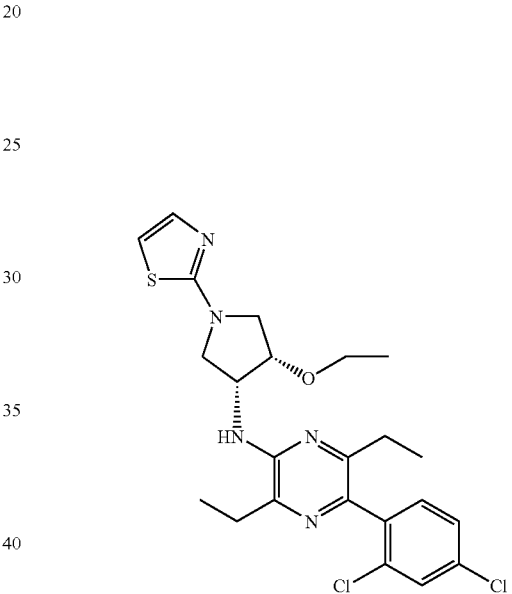

To a solution of 5-(2,4-dichlorophenyl)-N-[(3R,4S)-4-ethoxypyrrolidin-3-yl]-3,6-diethylpyrazin-2-amine (120 mg) in ethylene glycol dimethyl ether (0.586 ml) was added 2-bromo-1,3-thiazole (0.040 ml, 1.5 eq.), Cesium carbonate (144 mg, 1.5 eq.), N-[2'-(dicyclohexylphosphino)-1,1'-biphenyl-2-yl]-N,N-dimethylamine (16 mg, 0.14 eq.) and Tris(dibenzylideneacetone)dipalladium (19 mg, 0.7 eq.). The reaction mixture was heated at 100° C. for 16 h, poured into saturated sodium bicarbonate (50 ml), extracted 2×50 ml of CH$_2$Cl$_2$, dried MgSO$_4$, filtered and concentrated. Purification via MPLC chromatography eluting with 10–30% ethyl acetate/heptane provided the title compound as an amorphous solid (77 mg, 50%): 1H NMR (400 MHz, CDCl$_3$) δ) 7.50, 7.34, 7.28–7.23, 6.53, 5.30, 4.92, 4.27, 4.02, 3.82–3.72, 3.55, 3.46, 2.72, 2.48, 1.33–1.27, 1.16; IR (liq.) 2972 (s), 2934, 2335 (w), 1564 (s), 1539 (s), 1494 (s), 1470 (s), 1396 (s), 1357, 1350, 1201, 1141, 1121 (s), 1101, 610 cm$^{-1}$ HRMS (ESI) calcd for C$_{23}$H$_{27}$N$_5$OSCl$_2$+H$_1$ 492.1391. found 492.1378.

Example 2

Preparation of 5-(2,4-dichlorophenyl)-N-[(3R,4S)-4-ethoxy-1-pyridin-2-ylpyrrolidin-3-yl]-3,6-diethylpyrazin-2-amine

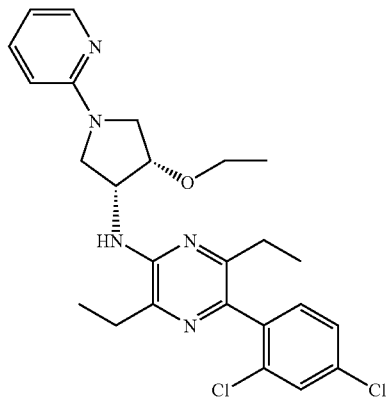

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 2-bromo pyridine provided the title compound as an amorphous solid: 1 H NMR (400 MHz, CDCl$_3$) δ) 8.20, 7.50, 7.32, 7.28, 6.69, 6.53, 5.33, 4.92, 4.28, 4.05, 3.92–3.78, 3.58, 3.42, 2.73, 2.50, 1.33–1.25,1.16; HRMS (ESI) calcd for C$_{25}$H$_{29}$N$_5$OCl$_2$+H$_1$ 486.1827. found 486.1827.

Example 3

Preparation of 5-(2,4-dichlorophenyl)-N-[(3R,4S)-4-ethoxy-1-pyridin-3-ylpyrrolidin-3-yl]-3,6-diethylpyrazin-2-amine

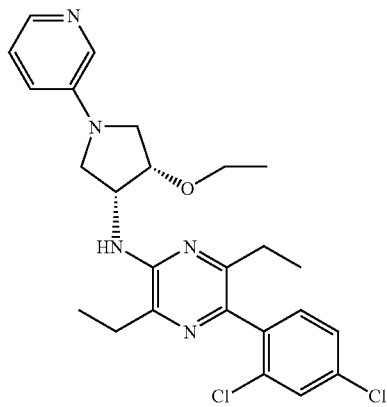

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 3-bromo pyridine provided the title compound as an amorphous solid: 1H NMR (400 MHz, CDCl$_3$) δ) 7.97, 7.51, 7.46, 7.33–7.28, 7.11, 5.31, 4.92, 4.31, 3.92, 3.85, 3.78–3.33, 2.73, 2.49, 1.35–1.29, 1.16; HRMS (ESI) calcd for C$_{25}$H$_{29}$N$_5$OCl$_2$+H$_1$ 486.1827. found 486.1834.

Example 4

Preparation of 5-(2,4-dichlorophenyl)-N-[(3R,4S)-4-ethoxy-1-pyridin-4-ylpyrrolidin-3-yl]-3,6-diethylpyrazin-2-amine

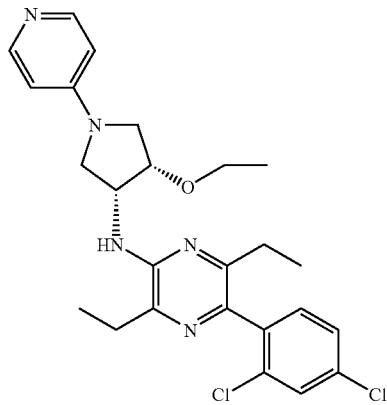

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 4-bromo pyridine provided the title compound as an amorphous solid: 1H NMR (400 MHz, CDCl$_3$) δ) 8.23, 7.50, 7.35, 7.28, 6.50, 5.30, 4.90, 4.29, 3.95, 3.76, 3.65–3.58, 3.42, 2.73, 2.49, 1.35–1.27, 1.16; IR (diffuse reflectance) 2971 (s), 2497 (w), 2388 (w), 2350 (w), 2338 (w), 2328 (w), 1596 (s), 1569, 1550 (s), 1516, 1508, 1499 (s), 1467 (s), 1397 (s), 1393 (s) cm$^{-1}$ HRMS (ESI) calcd for C$_{25}$H$_{29}$N$_5$OCl$_2$+H$_1$ 486.1827. found 486.1810.

Example 5

Preparation of 5-(2,4-dichlorophenyl)-N-[(3R,4S)-4-ethoxy-1-pyrimidin-2-ylpyrrolidin-3-yl]-3,6-diethylpyrazin-2-amine

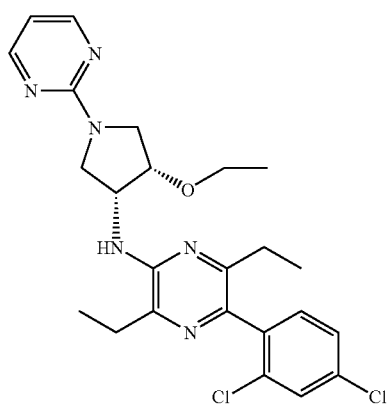

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 2-bromo pyrimidine provided the title compound as an amporphous solid: 1H NMR (400 MHz, CDCl$_3$) δ) 8.38, 7.50, 7.32, 7.26, 6.56, 5.30, 4.91, 4.25, 3.94, 3.76, 3.55, 2.73, 2.47, 1.33–1.26, 1.16; HRMS (ESI) calcd for C$_{24}$H$_{28}$N$_6$OCl$_2$+H$_1$ 487.1780. found 487.1770.

Example 6

Preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine

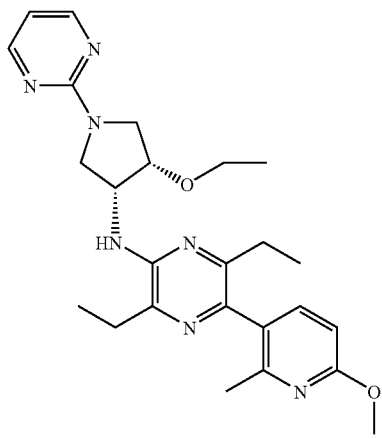

To a solution of N-[(3R,4S)-4-ethoxypyrrolidin-3-yl]-3,6-diethyl-5-(6-methoxy-2-methylpyridin-3-yl)pyrazin-2-amine (112 mg) in dioxane (1.45 ml) was added 2-bromopyrimidine (69 mg, 1.5 eq.), 1,3 Bis(2,6-di-i-propylphenyl) imidazolium chloride (20 mg, 0.16 eq.), Tris(dibenzylideneacetone)dipalladium (21 mg, 0.8 eq.) and potassium t-butoxide (49 mg, 1.5 eq.). The reaction mixture was heated at 100° C. for 16 h, poured into saturated sodium bicarbonate (50 ml), extracted 2×50 ml of CH$_2$Cl$_2$, dried MgSO$_4$, filtered and concentrated. Purification via MPLC chromatography eluting with 20–50% ethyl acetate/heptane provided the title compound as an amorphous solid (70 mg, 52%):

1H NMR (400 MHz, CDCl$_3$) δ) 8.36, 7.42, 6.63, 6.54, 5.24, 4.90, 4.24, 3.97, 3.92, 3.81–3.74, 3.57–3.46, 2.71, 2.47, 2.29, 1.33–1.26, 1.15; IR (liq.) 2972, 2397 (w), 2307 (w), 2214 (w), 2019 (w), 1945 (w), 1585 (s), 1565 (s), 1548 (s), 1510 (s), 1474 (s), 1395, 1384, 1304 (s), 1042 cm$^{-1}$ HRMS (ESI) calcd for C$_{25}$H$_{33}$N$_7$O$_2$+H$_1$ 464.2774. found 464.2766.

Example 7

Preparation of N-[(3R,4S)-4-ethoxy-1-pyridin-2-ylpyrrolidin-3-yl]-3,6-diethyl-5-(6-methoxy-2-methylpyridin-3-yl)pyrazin-2-amine

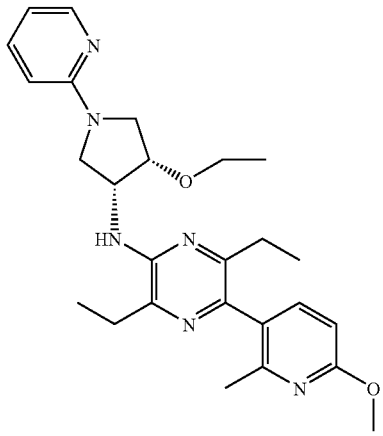

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromo pyridine provided the title compound as an amporphous solid:

1H NMR (400 MHz, CDCl$_3$) δ) 8.20, 7.50, 7.42, 6.65, 6.60, 6.43, 5.28, 4.90, 4.26, 4.04, 3.97, 3.79–3.75, 3.56, 3.41, 2.73, 2.48, 2.29, 1.33–1.26, 1.15; IR (diffuse reflectance) 2358 (w), 2018 (w), 1933 (w), 1598 (s), 1561, 1494, 1472 (s), 1443, 1392, 1360, 1303, 1250, 1122, 1041, 769 cm$^{-1}$ HRMS (ESI) calcd for C$_{26}$H$_{34}$N$_6$O$_2$+H$_1$ 463.2821. found 463.2816.

Example 8

Preparation of N-[(3R,4S)-4-ethoxy-1-(1,3-thiazol-2-yl)pyrrolidin-3-yl]-3,6-diethyl-5-(6-methoxy-2-methylpyridin-3-yl)pyrazin-2-amine

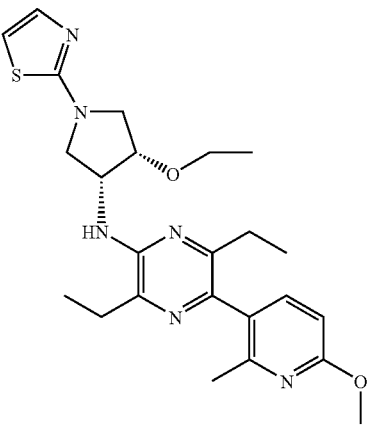

Following the procedure for the preparation of N-[(3R,4S)4-ethoxy-1-pyrimidin-2-ylpyrrolidin-3-yl]-3,6-diethyl-5-(6-methoxy-2-methylpyridin-3-yl)pyrazin-2-amine but substituting 2-bromo-1,3-thiazole provided the title compound as an amporphous solid:

1H NMR (400 MHz, CDCl$_3$) δ) 7.42, 7.25, 6.65, 6.54, 5.24, 4.92, 4.27, 4.02, 3.97, 3.88–3.79, 3.56–3.46, 2.70, 2.48, 2.29, 1.33–1.27, 1.15; IR (liq.) 2972, 2410 (w), 2237 (w), 2019 (w), 1972 (w), 1596 (s), 1563 (s), 1540 (s), 1493 (s), 1474 (s), 1426, 1395 (s), 1304 (s), 1251, 1042 cm$^{-1}$ HRMS (ESI) calcd for $C_{24}H_{32}N_6O_2S+H_1$ 469.2386. found 469.2375.

Example 9

Preparation of 5-[6-(dimethylamino)-4-methylpyridin-3-yl]-N-[(3R,4S)-4-ethoxy-1-pyridin-2-ylpyrrolidin-3-yl]-3,6-diethylpyrazin-2-amine

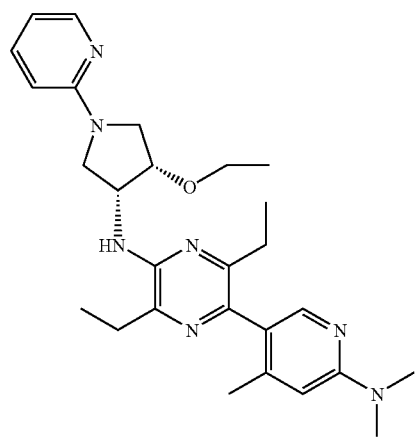

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromo pyridine and 5-[6-(dimethylamino)-4-methylpyridin-3-yl]-N-[(3R,4S)-4-ethoxypyrrolidin-3-yl]-3,6-diethylpyrazin-2-amine provided the title compound as an amporphous solid: $^1$H NMR (400 MHz, CDCl$_3$) δ) 8.19, 7.99, 7.47, 6.58, 6.46, 6.41, 5.25, 4.90, 4.25, 4.02, 3.80–3.72, 3.55, 3.40, 3.13, 2.70, 2.54, 2.12, 1.29, 1.16; IR (liq.) 2969, 2930, 2871, 2414 (w), 1941 (w), 1602 (s), 1558 (s), 1490 (s), 1474 (s), 1443 (s), 1395 (s), 1374, 1166, 1124, 770 cm$^{-1}$ HRMS (ESI) calcd for $C_{27}H_{37}N_7O+H_1$ 476.3138. found 476.3134.

Example 10

Preparation of 5-[6-(dimethylamino)-4-methylpyridin-3-yl]-N-[(3R,4S)-4-ethoxy-1-pyrimidin-2-ylpyrrolidin-3-yl]-3,6-diethylpyrazin-2-amine

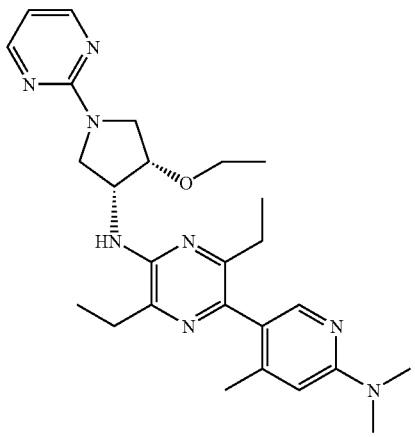

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 5-[6-(dimethylamino)-4-methylpyridin-3-yl]-N-[(3R,4S)-4-ethoxypyrrolidin-3-yl]-3,6-diethylpyrazin-2-amine provided the title compound as an amporphous solid: $^1$H NMR (400 MHz, CDCl$_3$) δ) 8.36, 7.99, 6.53, 6.46, 5.19, 4.91, 4.22, 3.95, 3.73, 3.58–3.44, 3.13, 2.71, 2.54, 2.12, 1.32–1.26, 1.16; IR (diffuse reflectance) 2969, 2931, 2403 (w), 2351 (w), 2306 (w), 2212 (w), 2168 (w), 1606 (s), 1583 (s), 1568 (b), 1547 (s), 1508 (s), 1474 (s), 1393 (s), 798 cm$^{-1}$ HRMS (ESI) calcd for $C_{26}H_{36}N_8O+H_1$ 477.3090. found 477.3113.

Example 11

Preparation of 5-[6-(dimethylamino)-4-methylpyridin-3-yl]-N-[(3R,4S)-4-ethoxy-1-(1,3-thiazol-2-yl)pyrrolidin-3-yl]-3,6-diethylpyrazin-2-amine

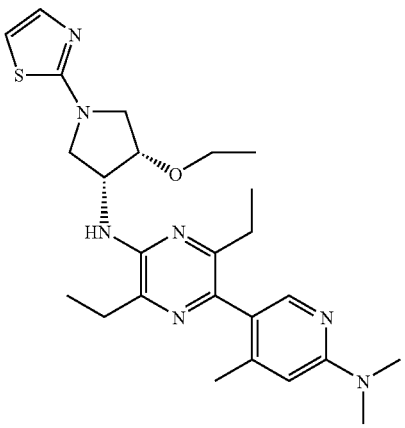

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromo-1,3-thiazole and 5-[6-(dimethylamino)-4-methylpyridin-3-yl]-N-[(3R,4S)-4-ethoxypyrrolidin-3-yl]-3,6-diethylpyrazin-2-amine provided the title compound as an amorphous solid: $^1$H NMR (400 MHz, CDCl$_3$) δ) 7.99, 7.23, 6.53, 6.46, 5.20, 4.92, 4.29, 4.02, 3.78, 3.58, 3.42, 3.13, 2.71, 2.53, 2.12, 1.33–1.27, 1.16; IR (diffuse reflectance) 2970, 2931, 2872, 2350 (w), 1606 (s), 1537 (s), 1489 (s), 1393 (s), 1372, 1360, 1347, 1343, 1338, 1210, 1122 cm$^{-1}$ HRMS (ESI) calcd for C$_{25}$H$_{35}$N$_7$OS+H$_1$ 482.2702. found 482.2699.

Example 12

Preparation of 5-(2-chloro-4-methoxyphenyl)-N-[(3R,4S)-4-ethoxy-1-(4-methoxypyrimidin-2-yl)pyrrolidin-3-yl]-3,6-diethylpyrazin-2-amine

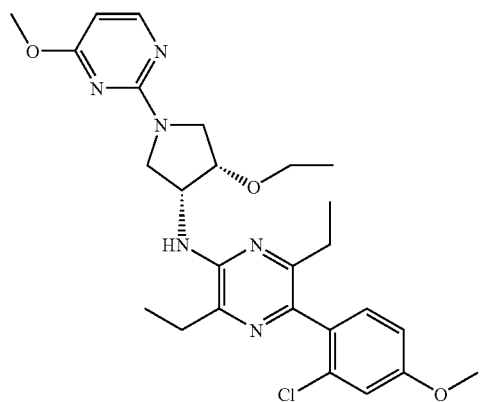

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 5-(2-chloro-4-methoxyphenyl)-N-[(3R,4S)-4-ethoxypyrrolidin-3-yl]-3,6-diethylpyrazin-2-amine and 2-chloro-4-methoxypyrimidine provided the title compound as an amorphous solid: $^1$H NMR (400 MHz, CDCl$_3$) δ) 8.03, 7.25, 7.02, 6.90, 6.02, 5.25, 4.88, 4.22, 3.92–3.78, 3.55, 2.74, 2.50, 1.33–1.26, 1.16; IR (diffuse reflectance) 2972, 2475 (w), 2350 (w), 2310 (w), 2183 (w), 2069 (w), 1585 (s), 1568 (s), 1516 (s), 1482 (s), 1466 (s), 1397, 1393, 1292, 1231 cm$^{-1}$ HRMS (ESI) calcd for C$_{26}$H$_{33}$N$_6$O$_3$Cl+H$_1$ 513.2380. found 513.2356.

Example 13

Preparation of 5-(2-chloro-4-methoxyphenyl)-N-[(3R,4S)-4-ethoxy-1-(4-methoxypyridin-2-yl)pyrrolidin-3-yl]-3,6-diethylpyrazin-2-amine hydrogen chloride

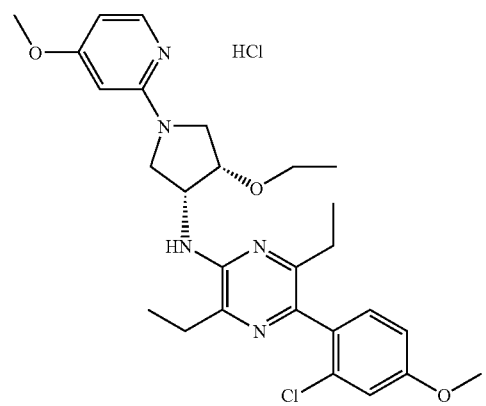

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 5-(2-chloro-4-methoxyphenyl)-N-[(3R,4S)-4-ethoxypyrrolidin-3-yl]-3,6-diethylpyrazin-2-amine and 2-chloro-4-methoxypyridine provided the title compound as an amorphous solid: $^1$H NMR (400 MHz, CDCl$_3$) δ 8.6, 8.08, 7.22, 7.12, 7.05, 6.90, 6.40, 5.92, 5.40, 5.00, 4.32, 4.20–4.10, 3.95, 3.86, 3.52, 2.81, 2.60, 1.33, 1.26, 1.18; IR (diffuse reflectance) 2966, 2934, 2685 (b), 2036 (w), 1974 (w), 1657, 1607 (s), 1493, 1463, 1442, 1404, 1293, 1265, 1232, 826 cm$^{-1}$ HRMS (ESI) calcd for C$_{27}$H$_{34}$N$_5$O$_3$Cl+H$_1$ 512.2429. found 512.2417.

Example 14

Preparation of 5-(2-chloro-4-methoxyphenyl)-N-[(3R,4S)-4-ethoxy-1-pyrimidin-2-ylpyrrolidin-3-yl]-3,6-diethyl pyrazin-2-amine

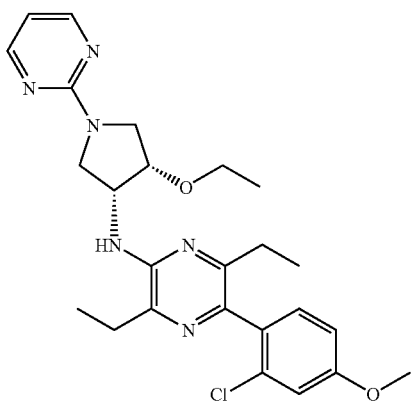

Following the procedure for the preparation of 5-(2,4-dichlorophenyl)-N-[(3R,4S)-4-ethoxy-1-(1,3-thiazol-2-yl)pyrrolidin-3-yl]-3,6-diethylpyrazin-2-amine but substituting 2-bromopyrimidine and starting with 5-(2-chloro-4-methoxyphenyl)-N-[(3R,4S)-4-ethoxypyrrolidin-3-yl]-3,6-diethylpyrazin-2-amine provided the title compound as an amorphous solid. $^1$H NMR (CDCl$_3$) δ 1.17, 1.26–1.34, 2.51, 2.76, 3.54, 3.78, 3.86, 3.97, 4.27, 4.91, 5.25, 6.61, 6.90, 7.02, 7.25, 8.40; IR (diffuse reflectance) 2971, 2392 (w), 2352 (w), 2307 (w), 2265 (w), 2170 (w), 1583 (s), 1569, 1549 (s), 1508 (s), 1481 (s), 1475 (s), 1397, 1392, 1384 cm$^{-1}$ HRMS (EI) calcd for C25H31ClN6O2 482.2197. found 482.2192.

Example 15

Preparation of 5-(2-chloro-4-methoxyphenyl)-N-[(3R,4S)-4-ethoxy-1-pyridin-2-ylpyrrolidin-3-yl]-3,6-diethyl pyrazin-2-amine

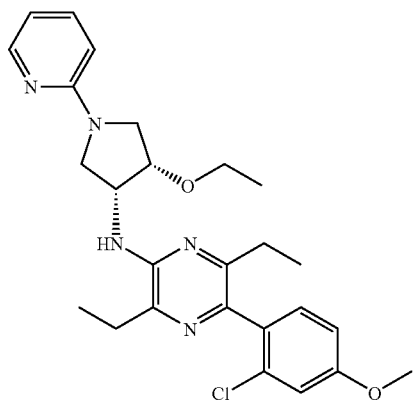

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromopyridine and 1,3-Bis(2,6-di-l-propylphenyl)-4,5-dihydro-imidzaolium tetrafluoroborate, and starting with 5-(2-chloro-4-methoxyphenyl)-N-[(3R,4S)-4-ethoxypyrrolidin-3-yl]-3,6-diethylpyrazin-2-amine provided the title compound as an amorphous solid. $^1$H NMR (CDCl$_3$) δ 1.17, 1.24–1.34, 2.51, 2.76, 3.56, 3.76, 3.86, 3.99, 4.25, 4.91, 5.25, 6.61, 6.90, 7.02, 7.25, 8.41; IR (diffuse reflectance) 2352 (w), 2340 (w), 2062 (w), 1940 (w), 1906 (w), 1600 (s), 1567, 1559, 1555, 1482 (s), 1474 (s), 1441 (s), 1392, 1287, 1229 cm$^{-1}$ HRMS (ESI) calcd for C26H32N5O2Cl+H1 482.2322. found 482.2332.

Example 16

Preparation of 5-(2-chloro-4-methoxyphenyl)-N-[(3R,4S)-4-ethoxy-1-pyridin-3-ylpyrrolidin-3-yl]-3,6-diethyl pyrazin-2-amine

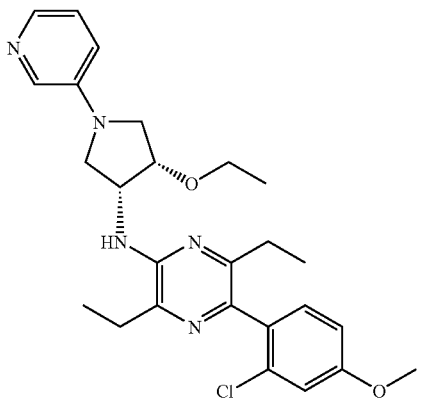

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrzin-2-amine but substituting 3-bromopyridine and starting with 5-(2-chloro-4-methoxyphenyl)-N-[(3R,4S)-4-ethoxypyrrolidin-3-yl]-3,6-diethylpyrazin-2-amine provided the title compound as an amorphous solid. $^1$H NMR (CDCl$_3$) δ 1.17, 1.26–1.33, 2.51, 2.73, 3.39, 3.57, 3.76, 3.78, 3.86, 3.93, 4.31, 4.91, 5.26, 6.89, 7.04, 7.25, 8.00; IR (diffuse reflectance) 2970, 2430 (w), 2054 (w), 1914 (w), 1603, 1584, 1566 (s), 1481 (s), 1434, 1396, 1372, 1287, 1228, 1122, 1044 cm$^{-1}$ HRMS (ESI) calcd for C26H32N5O2Cl+H1 482.2322. found 482.2311.

Example 17

Preparation of 5-(2-chloro-4-methoxyphenyl)-N-[(3R,4S)-4-ethoxy-1-(1,3-thiazol-2-yl)pyrrolidin-3-yl]-3,6-diethylpyrazin-2-amine

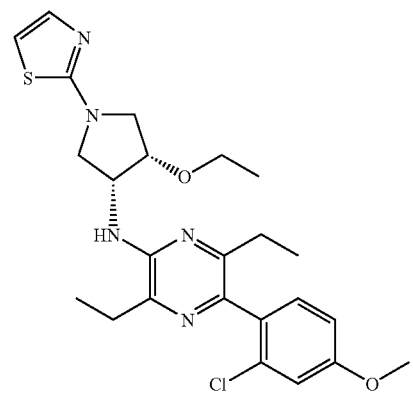

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but starting with 5-(2-chloro-4-methoxyphenyl)-N-[(3R,4S)-4-ethoxypyrrolidin-3-yl]-3,6-diethylpyrazin-2-amine provided the title compound as an amorphous solid. $^1$H NMR (CDCl$_3$) δ 1.17, 1.25~1.35, 2.50, 2.72, 3.45, 3.58, 3.75, 3.86, 4.04, 4.27, 4.93, 5.26, 6.55, 6.90, 7.02, 7.24; IR (diffuse reflectance) 2970, 2351 (w), 2337 (w), 2063 (w), 1604, 1568, 1549 (s), 1537 (s), 1482 (s), 1397, 1359, 1286, 1228, 1199, 1043 cm$^{-1}$ HRMS (ESI) calcd for C24H30N5O2SCl+H1 488.1887. found 488.1880.

Example 18

Preparation of N-[(3R,4S)-4-ethoxy-1-pyrimidin-2-ylpyrrolidin-3-yl]-3,6-diethyl-5-(4-methoxy-2-methylphenyl)pyrazin-2-amine

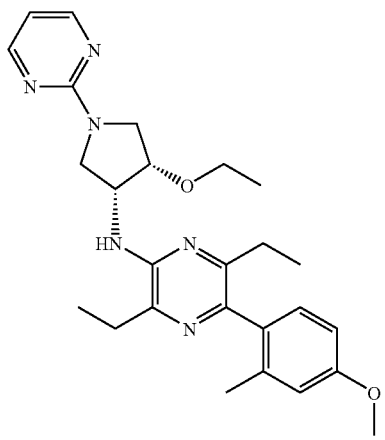

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but substituting 2-bromopyrimidine and starting with N-[(3R,4S)-4-ethoxypyrrolidin-3-yl]-3,6-diethyl-5-(4-methoxy-2-methylphenyl)pyrazin-2-amine provided the title compound as an amorphous solid. $^1$H NMR (CDCl$_3$) δ 1.15, 1.28, 2.13, 2.48, 2.74, 3.51, 3.77, 3.85, 3.98, 4.25, 4.90, 5.20, 6.56, 6.81, 7.12, 8.37; IR (diffuse reflectance) 2970, 2402 (w), 2350 (w), 2307 (w), 2212 (w), 2169 (w), 1583 (s), 1568, 1548 (s), 1508 (s), 1475 (s), 1393, 1383, 1242, 798 cm$^{-1}$ HRMS (ESI) calcd for C26H34N6O2+H1 463.2821. found 463.2816.

Example 19

Preparation of N-[(3R,4S)-4-ethoxy-1-pyridin-2-ylpyrrolidin-3-yl]-3,6-diethyl-5-(4-methoxy-2-methylphenyl)pyrazin-2-amine

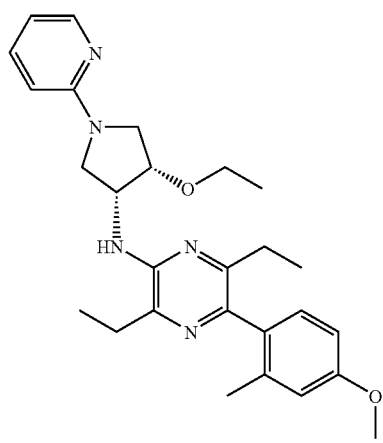

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrzin-2-amine but substituting 2-bromopyridine and starting with N-[(3R,4S)-4-ethoxypyrrolidin-3-yl]-3,6-diethyl-5-(4-methoxy-2-methylphenyl)pyrazin-2-amine provided the title compound as an amorphous solid. $^1$H NMR (CDCl$_3$) δ 1.15, 1.31, 2.14, 2.49, 2.71, 3.42, 3.54, 3.78, 3.85, 4.07, 4.28, 4.92, 5.21, 6.50~6.66, 6.79, 6.84, 7.12, 8.20; IR (diffuse reflectance) 2969, 2405 (w), 2351 (w), 2337 (w), 2212 (w), 2015 (w), 1599 (s), 1560, 1482 (s), 1474 (s), 1442 (s), 1392, 1385, 1242, 769 cm$^{-1}$ HRMS (ESI) calcd for C27H35N5O2+H1 462.2869. found 462.2859.

Example 20

Preparation of N-[(3R,4S)-4-ethoxy-1-(1,3-thiazol-2-yl)pyrrolidin-3-yl]-3,6-diethyl-5-(4-methoxy-2-methylphenyl)pyrazin-2-amine

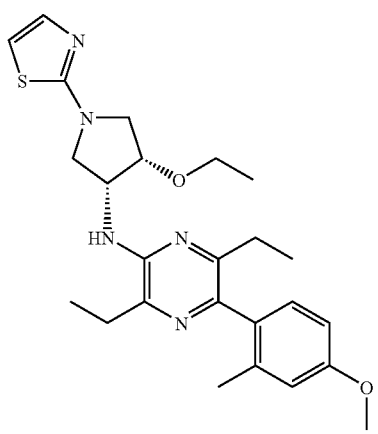

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but starting with N-[(3R,4S)-4-ethoxypyrrolidin-3-yl]-3,6-diethyl-5-(4-methoxy-2-methylphenyl)pyrazin-2-amine provided the title compound as an amorphous solid. $^1$H NMR (CDCl$_3$) δ 1.15, 1.31, 2.13, 2.47, 2.71, 3.45~3.59, 3.77, 3.85, 4.03, 4.28, 4.93, 5.21, 6.54, 6.81, 6.83, 7.11, 7.26; IR (diffuse reflectance) 2970, 2932, 2403 (w), 2350 (w), 2334 (w), 2212 (w), 1965 (w), 1608, 1537 (s), 1482 (s), 1393, 1294, 1242, 1200, 1165 cm$^{-1}$ HRMS (ESI) calcd for C25H33N5O2S+H1 468.2433. found 468.2416.

Example 21

Preparation of N-[(3R,4S)-4-ethoxy-1-pyrimidin-2-yl pyrrolidin-3-yl]-3,6-diethyl-5-[6-methoxy-2-(trifluoromethyl)pyridin-3-yl]pyrazin-2-amine

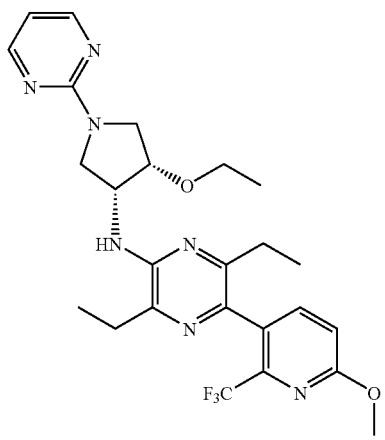

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but substituting 2-bromopyrimidine and starting with N-[(3R,4S)-4-ethoxypyrrolidin-3-yl]-3,6-diethyl-5-[6-methoxy-2-(trifluoromethyl)pyridin-3-yl]pyrazin-2-amine provided the title compound as an amorphous solid. $^1$H NMR (CDCl$_3$) δ 1.15, 1.30, 2.43, 2.69, 3.53, 3.78, 3.87, 3.99, 4.04, 4.27, 4.91, 5.27, 6.61, 6.97, 7.56, 8.41; IR (diffuse reflectance) 2398 (w), 2352 (w), 2307 (w), 2214 (w), 2173 (w), 1584 (s), 1569, 1549 (s), 1508 (s), 1476 (s), 1397, 1341, 1277, 1175, 1137 (s) cm$^{-1}$ HRMS (ESI) calcd for C25H30N7O2F3+H1 518.2491. found 518.2479.

Example 22

Preparation of N-[(3R,4S)-4-ethoxy-1-pyridin-2-yl pyrrolidin-3-yl]-3,6-diethyl-5-[6-methoxy-2-(trifluoromethyl)pyridin-3-yl]pyrazin-2-amine

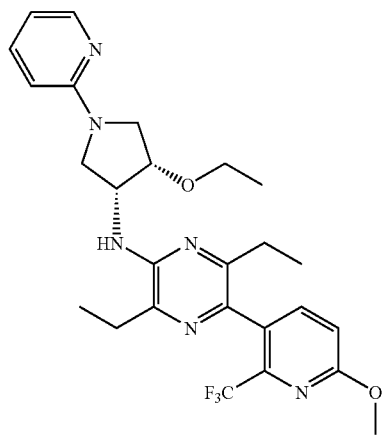

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but substituting 2-bromopyridine and starting with N-[(3R,4S)-4-ethoxypyrrolidin-3-yl]-3,6-diethyl-5-[6-methoxy-2-(trifluoromethyl)pyridin-3-yl]pyrazin-2-amine provided the title compound as an amorphous solid. $^1$H NMR (CDCl$_3$) δ 1.15, 1.30, 2.44, 2.70, 3.43, 3.58, 3.75~3.85, 4.05, 4.27, 4.90, 5.32, 6.46, 6.62, 6.97, 7.52, 7.56, 8.20; IR (diffuse reflectance) 2352 (w), 2338 (w), 2257 (w), 2175 (w), 2025 (w), 1600 (s), 1559, 1475 (s), 1443 (s), 1397, 1339, 1277, 1239, 1174, 1137 (s) cm$^{-1}$ HRMS (ESI) calcd for C26H31N6O2F3+H1 517.2538. found 517.2533.

Example 23

Preparation of N-[(3R,4S)-4-ethoxy-1-(1,3-thiazol-2-yl)pyrrolidin-3-yl]-3,6-diethyl-5-[6-methoxy-2-(trifluoromethyl)pyridin-3-yl]pyrazin-2-amine

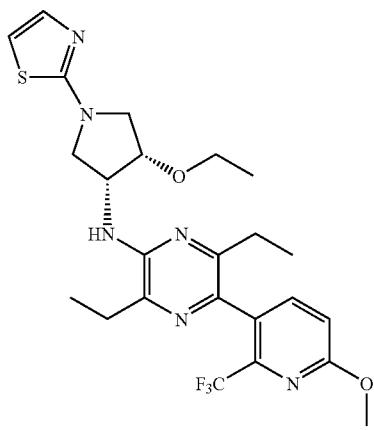

Following the procedure for the preparation of 5-(2,4-dichlorophenyl)-N-[(3R,4S)-4-ethoxy-1-(1,3-thiazol-2-yl)pyrrolidin-3-yl}-3,6-diethylpyrazin-2-amine but starting with N-[(3R,4S)-4-ethoxypyrrolidin-3-yl]-3,6-diethyl-5-[6-methoxy-2-(trifluoromethyl)pyridin-3-yl]pyrazin-2-amine provided the title compound as an amorphous solid. $^1$H NMR (CDCl$_3$) δ 1.15, 1.30, 2.45, 2.68, 3.48~3.58, 3.77, 3.88, 4.04, 4.29, 4.94, 5.29, 6.56, 6.98, 7.56; IR (diffuse reflectance) 2974, 2350 (w), 2337 (w), 1921 (w), 1607, 1568, 1538 (s), 1477 (s), 1397, 1342, 1278 (s), 1239, 1192, 1175, 1137 (s) cm$^{-1}$ HRMS (ESI) calcd for C24H29N6O2SF3+H1 523.2103. found 523.2108.

Example 24

Preparation of 5-(2,6-dimethoxypyridin-3-yl)-N-[(3R,4S)-4-ethoxy-1-pyridin-2-ylpyrrolidin-3-yl]-3,6-diethylpyrazin-2-amine hydrogen chloride

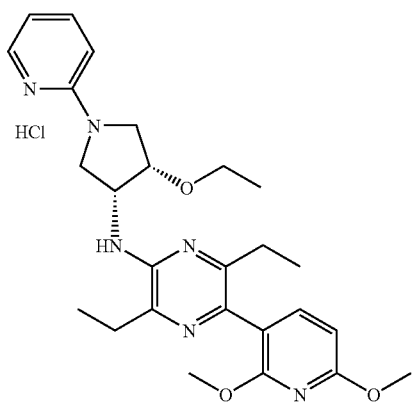

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromopyridine and starting with 5-(2,6-dimethoxypyridin-3-yl)-N-[(3R,4S)-4-ethoxypyrrolidin-3-yl]-3,6-diethylpyrazin-2-amine provided the title compound as an amorphous solid. $^1$H NMR (400 MHz, CDCl$_3$) δ 8.22, 7.81, 7.54, 6.83, 6.74, 6.43, 5.19, 4.95, 4.33, 4.15, 4.97, 3.93, 3.82, 3.57, 3.48, 2.72, 2.53, 1.34–1.26, 1.17; IR (diffuse reflectance) 2972, 2340 (w), 2022 (w), 1930 (w), 1646, 1602 (s), 1576, 1481, 1466, 1401, 1376, 1314, 1240, 1022, 765 cm$^{-1}$ HRMS (ESI) calcd for C26H34N6O3+H1 479.2770. found 479.2765. Anal. Calcd for C$_{26}$H$_{34}$N$_6$O$_3$. HCl: C, 60.63; H, 6.85; N, 16.32; Cl, 6.88. Found: C, 60.66; H, 6.91; N, 16.03.

Example 25

Preparation of 5-(2,6-dimethoxypyridin-3-yl)-N-[(3R,4S)-4-ethoxy-1-(1,3-thiazol-2-yl)pyrrolidin-3-yl]-3,6-diethylpyrazin-2-amine

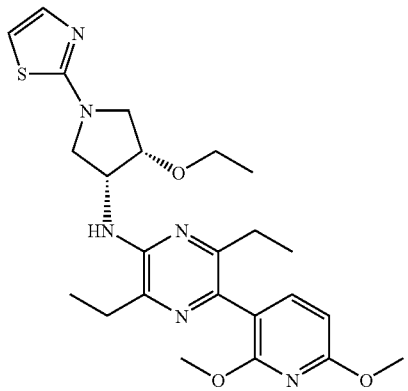

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromothiazole and starting with 5-(2,6-dimethoxypyridin-3-yl)-N-[(3R,4S)-4-ethoxypyrrolidin-3-yl]-3,6-diethylpyrazin-2-amine provided the title compound as an amorphous solid. $^1$H NMR (400 MHz, CDCl$_3$) δ 7.54, 7.23, 6.52, 6.43, 5.21, 4.92, 4.25, 4.00, 3.97, 3.93, 3.80–3.73, 3.54, 3.44, 2.72, 2.52, 1.33–1.26, 1.18; IR (diffuse reflectance) 2963, 2327 (w), 2187 (w), 2056 (w), 1997 (w), 1604, 1580, 1567, 1538 (s), 1474 (s), 1397, 1377, 1311, 1235, 1031 cm$^{-1}$ HRMS (ESI) calcd for C24H32N6O3S+H1 485.2335. found 485.2333.

Example 26

Preparation of 5-(2,6-dimethoxypyridin-3-yl)-N-[(3R,4S)-4-ethoxy-1-pyrimidin-2-ylpyrrolidin-3-yl]-3,6-diethylpyrazin-2-amine

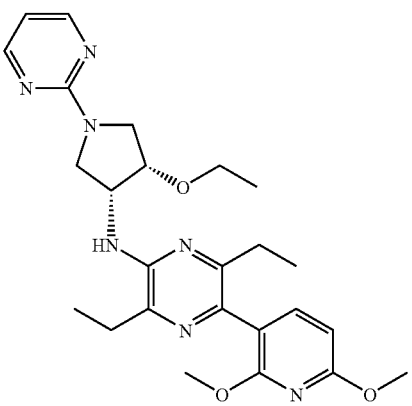

Following the procedure for the preparation of N-[(3R,4S)-4-ethoxy-1-pyrimidin-2-ylpyrrolidin-3-yl]-3,6-diethyl-5-(6-methoxy-2-methylpyridin-3-yl)pyrazin-2-amine but substituting 2-bromopyrimidine and starting with 5-(2,6-dimethoxypyridin-3-yl)-N-[(3R,4S)4-ethoxypyrrolidin-3-yl]-3,6-diethylpyrazin-2-amine provided the title compound as an amorphous solid. $^1$H NMR (400 MHz, CDCl$_3$) δ) 8.35, 7.53, 6.52, 6.42, 5.18, 4.90, 4.20, 3.97, 3.93, 3.89, 3.77, 3.52, 2.72, 2.52, 1.33–1.25, 1.18; IR (diffuse reflectance) 2402 (w), 2347 (w), 2307 (w), 2264 (w), 2194 (w), 1601, 1582 (s), 1566, 1547 (s), 1510 (s), 1474 (s), 1395, 1377 (s), 1312 (s), 1022 cm$^{-1}$ HRMS (ESI) calcd for C25H33N7O3+H1 480.2723. found 480.2715.

Example A in vitro CRF$_1$ Receptor Binding Assay for the Evaluation of Biological Activity The following is a description of a standard in vitro binding assay for the evaluation of biological activity of a test compound on CRF$_1$ receptors. It is based on a modified protocol described by De Souza (De Souza, 1987).

The binding assay utilizes brain membranes, commonly from rats. To prepare brain membranes for binding assays, rat frontal cortex is homogenized in 10 mL of ice cold tissue buffer (50 mM HEPES buffer pH 7.0, containing 10 mM MgCl$_2$, 2 mM EGTA, 1 µg/mL aprotinin, 1 µg/mL leupeptin and 1 µg/mL pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 µg/mL.

Binding assays are performed in 96 well plates at a final volume of 300 µL. The assays are initiated by the addition of 150 µL membrane suspension to 150 µL of assay buffer containing $^{125}$I-ovine-CRF (final concentration 150 pM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvester. Filters are washed three times with ice cold phosphate buffered saline pH 7.0 containing 0.01% Triton X-100. Filters are assessed for radioactivity in a Packard TopCount.

Alternatively, tissues and cells that naturally express CRF receptors, such as IMR-32 human neuroblastoma cells (ATCC; Hogg et al., 1996), can be employed in binding assays analogous to those described above.

A compound is considered to be active if it has a Ki value of less than about 10 µM for the inhibition of CRF. Non-specific binding is determined in the presence of excess (10 µM) α-helical CRF.

Example B

Ex vivo CRF$_1$ Receptor Binding Assay for the Evaluation of Biological Activity The following is a description of a typical ex vivo CRF$_1$ receptor binding assay for assessing the biological activity of a test compound on CRF$_1$ receptors.

Fasted, male, Harlen-bred, Sprague-Dawley rats (170–210 g) were orally dosed with test compound or vehicle, via gastric lavage between 12:30 and 2:00 PM. Compounds were prepared in vehicle (usually 10% soybean oil, 5% polysorbate 80, in dH20). Two hours after drug administration, rats were sacrificed by decapitation, frontal cortices were quickly dissected and placed on dry ice, then frozen at −80° C. until assayed; trunk blood was collected in heparinized tubes, plasma separated by centrifugation (2500 RPM's for 20 minutes), and frozen at −20° C.

On the day of the binding assay, tissue samples were weighed and allowed to thaw in ice cold 50 mM Hepes buffer (containing 10 mM MgCl$_2$, 2 mM EGTA, 1 µg/mL aprotinin, 1 µg/mL leupeptin hemisulfate, and 1 µg/mL pepstatin A, 0.15 mM bacitracin, and 0.1% ovalalbumin, pH=7.0 at 23° C.) and then homogenized for 30 sec at setting 5 (Polytron by Kinematica). Homogenates were incubated (two hours, 23° C., in the dark) with [$^{125}$I] CRF (0.15 nM, NEN) in the presence of assay buffer (as described above) or DMP-904 (10 uM). The assay was terminated by filtration (Packard FilterMate, GF/C filter plates); plates were counted in Packard TopCount LSC; total and non-specific fmoles calculated from DPM's. Data are expressed as % of vehicle controls (specific fmoles bound). Statistical significance was determined using student's t-test.

Example C

Inhibition of CRF Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Example D in vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J.

Dunn Brain Research Reviews 15:71 (1990). A compound may be tested in any species of rodent or small mammal.

What is claimed is:

1. A compound of Formula I,

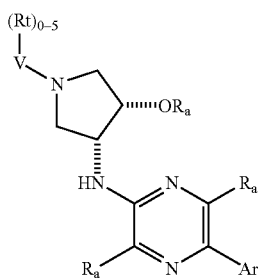

Formula I or a stereoisomer thereof, or a pharmaceutically acceptable salt thereof, wherein in Formula I, Ar is selected from aryl, substituted aryl, heteroaryl, or substituted heteroaryl;

V is heteroaryl or phenyl, wherein heteroaryl and phenyl are optionally substituted with 1–5 of $R_t$;

$R_a$ each is independently selected from H, alkyl, cycloalkyl, haloalkyl, aryl, heteroaryl, or heterocycloalkyl, wherein alkyl, cycloalkyl, haloalkyl, aryl, heteroaryl, and heterocycloalkyl is optionally substituted with 1 to 5 of $R_t$, —Oalkyl, —S(O)$_m$$R_t$, NR$_t$R$_t$, oxo (=O), thione (=S), phenyl, heteroaryl, or heterocycloalkyl;

$R_t$ each is independently selected from H, halogen, —NO$_2$, —NH$_2$, —OH, —SH, —CN, —C(O)NH$_2$, —C(O)—NHalkyl, —C(O)Nalkylalkyl, —Oalkyl, —Ohaloalkyl, NHalkyl, Nalkylalkyl, —S(O)$_m$alkyl, SO$_2$NH$_2$, SO$_2$Nhalkyl, SO$_2$Nalkylalkyl, alkyl, cycloalkyl, haloalkyl, phenyl, benzyl, heteroaryl, or heterocycloalkyl; and m is 0, 1 or 2.

2. A compound of claim 1, which is selected from the group consisting of:

5-(2,4-dichlorophenyl)-N-[(3R,4S)-4-ethoxy-1-(1,3-thiazol-2-yl)pyrrolidin-3-yl]-3,6-diethylpyrazin-2-amine, 5-(2,4-dichlorophenyl)-N-[(3R,4S)-4-ethoxy-1-pyridin-2-ylpyrrolidin-3-yl]-3,6-diethylpyrazin-2-amine, 5-(2,4-dichlorophenyl)-N-[(3R,4S)4-ethoxy-1-pyridin-3-ylpyrrolidin-3-yl]-3,6-diethylpyrazin-2-amine, 5-(2,4-dichlorophenyl)-N-[(3R,4S)-4-ethoxy-1-pyridin-4-ylpyrrolidin-3-yl]-3,6-diethylpyrazin-2-amine, 5-(2,4-dichlorophenyl)-N-[(3R,4S)4-ethoxy-1-pyrimidin-2-ylpyrrolidin-3-yl]-3,6-diethylpyrazin-2-amine, N-[(3R,4S)-4-ethoxy-1-pyrimidin-2-ylpyrrolidin-3-yl]-3,6-diethyl-5-(6-methoxy-2-methylpyridin-3-yl)pyrazin-2-amine, N-[(3R,4S)-4-ethoxy-1-pyridin-2-ylpyrrolidin-3-yl]-3,6-diethyl-5-(6-methoxy-2-methylpyridin-3-yl)pyrazin-2-amine, N-[(3R,4S)-4-ethoxy-1-(1,3-thiazol-2-yl)pyrrolidin-3-yl]-3,6-diethyl-5-(6-methoxy-2-methylpyridin-3-yl)pyrazin-2-amine, 5-[6-(dimethylamino)-4-methylpyridin-3-yl]-N-[(3R,4S)-4-ethoxy-1-pyridin-2-ylpyrrolidin-3-yl]-3,6-diethylpyrazin-2-amine 5-[6-(dimethylamino)-4-methylpyridin-3-yl]-N-[(3R,4S)-4-ethoxy-1-pyrimidin-2-ylpyrrolidin-3-yl]-3,6-diethylpyrazin-2-amine 5-[6-(dimethylamino)-4-methylpyridin-3-yl]-N-[(3R,4S)-4-ethoxy-1-(1,3-thiazol-2-yl)pyrrolidin-3-yl]-3,6-diethylpyrazin-2-amine 5-(2-chloro-4-methoxyphenyl)-N-[(3R,4S)-4-ethoxy-1-(4-methoxypyrimidin-2-yl)pyrrolidin-3-yl]-3,6-diethylpyrazin-2-amine 5-(2-chloro-4-methoxyphenyl)-N-[(3R,4S)-4-ethoxy-1-(4-methoxypyridin-2-yl)pyrrolidin-3-yl]-3,6-diethylpyrazin-2-amine hydrogen chloride 5-(2-chloro-4-methoxyphenyl)-N-[(3R,4S)-4-ethoxy-1-pyrimidin-2-ylpyrrolidin-3-yl]-3,6-diethylpyrazin-2-amine 5-(2-chloro-4-methoxyphenyl)-N-[(3R,4S)-4-ethoxy-1-pyridin-2-ylpyrrolidin-3-yl]-3,6-diethylpyrazin-2-amine 5-(2-chloro-4-methoxyphenyl)-N-[(3R,4S)-4-ethoxy-1-pyridin-3-ylpyrrolidin-3-yl]-3,6-diethylpyrazin-2-amine 5-(2-chloro-4-methoxyphenyl)-N-[(3R,4S)-4-ethoxy-1-(1,3-thiazol-2-yl)pyrrolidin-3-yl]-3,6-diethylpyrazin-2-amine N-[(3R,4S)-4-ethoxy-1-pyrimidin-2-ylpyrrolidin-3-yl]-3,6-diethyl-5-(4-methoxy-2-methylphenyl)pyrazin-2-amine N-[(3R,4S)-4-ethoxy-1-pyridin-2-ylpyrrolidin-3-yl]-3,6-diethyl-5-(4-methoxy-2-methylphenyl)pyrazin-2-amine N-[(3R,4S)-4-ethoxy-1-(1,3-thiazol-2-yl)pyrrolidin-3-yl]-3,6-diethyl-5-(4-methoxy-2-methylphenyl)pyrazin-2-amine N-[(3R,4S)-4-ethoxy-1-pyrimidin-2-ylpyrrolidin-3-yl]-3,6-diethyl-5-[6-methoxy-2-(trifluoromethyl)pyridin-3-yl]pyrazin-2-amine N-[(3R,4S)-4-ethoxy-1-pyridin-2-yl pyrrolidin-3-yl]-3,6-diethyl-5-[6-methoxy-2-(trifluoromethyl)pyridin-3-yl]pyrazin-2-amine N-[(3R,4S)-4-ethoxy-1-(1,3-thiazol-2-yl)pyrrolidin-3-yl]-3,6-diethyl-5-[6-methoxy-2-(trifluoromethyl)pyridin-3-yl]pyrazin-2-amine 5-(2,6-dimethoxypyridin-3-yl)-N-[(3R,4S)-4-ethoxy-1-pyridin-2-ylpyrrolidin-3-yl]-3,6-diethylpyrazin-2-amine hydrogen chloride 5-(2,6-dimethoxypyridin-3-yl)-N-[(3R,4S)-4-ethoxy-1-(1,3-thiazol-2-yl)pyrrolidin-3-yl]-3,6-diethylpyrazin-2-amine 5-(2,6-dimethoxypyridin-3-yl)-N-[(3R,4S)-4-ethoxy-1-pyrimidin-2-ylpyrrolidin-3-yl]-3,6-diethylpyrazin-2-amine.

3. A compound of claim 1 or 2 wherein, in an in vitro CRF receptor-binding assay using IMR-32 human neuroblastoma cells, the compound exhibits a Ki value of 1 micromolar or less.

4. A compound of claim 3 wherein the compound exhibits a Ki value of 100 nanomolar or less.

5. A prodrug which has a biohydrolyzable group selected from the group consisting of an amide, ester, carbamate, carbonate, acetate, formate, and benzoate derivative of an alcohol or an amino group of a compound of Formula I,

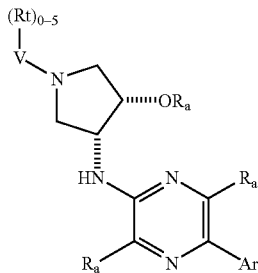

Formula I wherein in Formula I,
Ar is selected from aryl, substituted aryl, heteroaryl, or substituted heteroaryl;
V is heteroaryl or phenyl, wherein heteroaryl and phenyl are optionally substituted with 1–5 of $R_t$;
$R_a$ each is independently selected from H, alkyl, cycloalkyl, haloalkyl, aryl, heteroaryl, or heterocycloalkyl, wherein alkyl, cycloalkyl, haloalkyl, aryl, heteroaryl, and heterocycloalkyl is optionally substituted with 1 to 5 of $R_t$, —Oalkyl, —S(O)$_m R_t$, NR$_t R_t$, oxo (=O), thione (=S), phenyl, heteroaryl, or heterocycloalkyl;
$R_t$ each is independently selected from H, halogen, —NO$_2$, —NH$_2$, —OH, —SH, —CN, —C(O)NH$_2$, —C(O)—NHalkyl, —C(O)Nalkylalkyl, —Oalkyl, —Ohaloalkyl, NHalkyl, Nalkylalkyl, —S(O)$_m$alkyl, SO$_2$NH$_2$, SO$_2$Nhalkyl, SO$_2$Nalkylalkyl, alkyl, cycloalkyl, haloalkyl, phenyl, benzyl, heteroaryl, or heterocycloalkyl; and
m is 0, 1 or 2.

6. A pharmaceutical composition comprising a compound of claim 1 or 2.

7. A method of inhibiting the binding of CRF to the CRF$_1$ receptor in vitro, the method comprising contacting, in the presence of CRF, a solution comprising a compound of claim 1 or 2 with cells expressing the CRF$_1$ receptor, wherein the compound is present in the solution at a concentration sufficient to reduce levels of CRF binding to the cells in vitro.

8. A method for treating a disorder in a mammal manifested by hypersecretion of CRF, comprising administering to the mammal a therapeutically effective amount of a compound of claim 1, and wherein the disorder is selected from anxiety-related disorders; post-traumatic stress disorder; drug or alcohol withdrawal symptoms; and bipolar disorders.

9. The method according to claim 8 wherein the disorder is selected from anxiety-related disorders; bipolar disorders; and post-traumatic stress disorder.

10. The method according to claim 9 wherein the disorder is selected from anxiety-related disorders, and wherein the anxiety-related disorder is generalized anxiety.

11. A method of promoting smoking cessation in a human, comprising administering to the human in need thereof an effective amount of a compound of claim 1 or 2.

12. A method for treating depression in a human, comprising administering to the human in need thereof a therapeutically effective amount of a compound of claim 1.

* * * * *